United States Patent
Kagawa et al.

(10) Patent No.: US 12,037,624 B2
(45) Date of Patent: Jul. 16, 2024

(54) **MUTANT OF *TRICHODERMA* FILAMENTOUS FUNGUS AND METHOD OF PRODUCING PROTEIN**

(71) Applicant: Toray Industries, Inc., Tokyo (JP)

(72) Inventors: Yusuke Kagawa, Kanagawa (JP); Shingo Hiramatsu, Kanagawa (JP); Katsushige Yamada, Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 17/263,685

(22) PCT Filed: Jul. 29, 2019

(86) PCT No.: PCT/JP2019/029563
§ 371 (c)(1),
(2) Date: Jan. 27, 2021

(87) PCT Pub. No.: WO2020/027010
PCT Pub. Date: Feb. 6, 2020

(65) Prior Publication Data
US 2021/0222221 A1 Jul. 22, 2021

(30) Foreign Application Priority Data
Jul. 30, 2018 (JP) ................ 2018-142425

(51) Int. Cl.
| C12P 21/02 | (2006.01) |
| C07K 14/37 | (2006.01) |
| C12N 1/14 | (2006.01) |
| C12R 1/885 | (2006.01) |

(52) U.S. Cl.
CPC ............ *C12P 21/02* (2013.01); *C07K 14/37* (2013.01); *C12N 1/145* (2021.05); *C12R 2001/885* (2021.05)

(58) Field of Classification Search
CPC ......... C12P 21/02; C12N 1/145; C07K 14/37; C12R 2001/885
See application file for complete search history.

(56) References Cited

U.S. PATENT DOCUMENTS

| 2013/0224864 A1 | 8/2013 | Dodge et al. |
| 2014/0094587 A1 | 4/2014 | Bodie et al. |
| 2014/0099721 A1 | 4/2014 | Bodie et al. |
| 2014/0127817 A1 | 5/2014 | Bodie et al. |
| 2014/0220689 A1 | 8/2014 | Bodie et al. |
| 2014/0315313 A1 | 10/2014 | Bodie et al. |
| 2020/0165647 A1 | 5/2020 | Kobayashi et al. |

FOREIGN PATENT DOCUMENTS

| JP | 2013-533751 A | 8/2013 | |
| JP | 2014-513529 A | 6/2014 | |
| JP | 2014-513530 A | 6/2014 | |
| JP | 2014-513531 A | 6/2014 | |
| JP | 2014-513532 A | 6/2014 | |
| JP | 2014-513533 A | 6/2014 | |
| WO | WO2012027580 A1 * | 10/2014 | ........... C12N 9/2434 |
| WO | 2017/170917 A1 | 10/2017 | |

OTHER PUBLICATIONS

Boehm, "Genetic analyses of adaptin function from yeast to mammals", Gene, vol. 286, Issue 2, Mar. 20, 2002, pp. 175-186. Retrieved from the Internet <URL: https://www.sciencedirect.com/science/article/pii/S0378111902004225> (Year: 2002).*
Gomez-Navarro, "Protein sorting at the ER-Golgi interface", Journal of Cell Biology, 2016, 215 (6): 769-778. Retrieved from the Internet <URL: https://rupress.org/jcb/article/215/6/769/46099/Protein-sorting-at-the-ER-Golgi-interfaceProtein> (Year: 2016).*
Martinez, "Genome sequencing and analysis of the biomass-degrading fungus *Trichoderma reesei* (syn. *Hypocrea jecorina*)" (2011) . Retrieved from the internet <URL: https://www.nature.com/articles/nbt1403> (Year: 2011).*
Betts, "Ch. 14: Amino Acid Properties and Consequences of Substitutions", From "Bioinformatics for Geneticists", ISBNs: 0-470-84393-4 (Year: 2003).*
Kirchhausen, "Adaptors for Clathrin-Mediated Traffic", Annual Review of Cell and Developmental Biology, 1999, 15:705-32. Retrieved from the Internet <URL: https://www.annualreviews.org/doi/10.1146/annurev.cellbio.15.1.705> (Year: 1999).*
United Kingdom Research Institute (UKRI), "Table 1: Clathrin and COP coats: subunit functions and domains". Retrieved from the Internet <URL: https://web.archive.org/web/20051029185237/https://www2.mrc-lmb.cam.ac.uk/groups/hmm/Adaptors/Table 1.htm> (Year: 2005).*
Uniprot: GORI78_HYPJQ (2011). <URL: https://www.uniprot.org/uniprot/GORI78> (Year: 2011).*

(Continued)

*Primary Examiner* — Louise W Humphrey
*Assistant Examiner* — Deepa Mishra
(74) *Attorney, Agent, or Firm* — DLA Piper LLP (US)

(57) ABSTRACT

A mutant of a *trichoderma* filamentous fungus has a mutation that results in lost or lowered function of a beta-adaptin large subunit, or a mutation in an amino acid sequence that forms the beta-adaptin large subunit. A method produces a protein while maintaining a low viscosity in a culture solution during culturing by using the mutant.

10 Claims, 6 Drawing Sheets

Specification includes a Sequence Listing.

(56) References Cited

OTHER PUBLICATIONS

SCORE Search results for SEQ ID No. 2 in U.S. Appl. No. 17/263,685 (Year: 2021).*
Ekaterina E. Heldwein et al., "Crystal structure of the clathrin adaptor protein 1 core," Proc. Natl. Acad. Sci. USA., 2004, vol. 101, pp. 14108-14113.
Extended European Search Report in the counterpart European Application No. EP 19844909.2 dated Mar. 25, 2022.
Nishida, H. et al.: "The early diverging ascomycetous budding yeast Saitoella complicate has three histone deacetylases belonging to the Clr6, Hos2, and Rpd3 lineages," *The Journal of General and Applied Microbiology*, vol. 60, No. 1, 2014, pp. 7-12.
Peterson, R. et al.: Trichoderma reesei RUT-C30—thirty years of strain improvement, *Microbiology*, vol. 158, No. 1, 2012, pp. 58-68.

* cited by examiner

SEQUENCE LISTING

<160> NUMBER OF SEQ ID NOS: 23

<210> SEQ ID NO 1
<211> LENGTH: 2589
<212> TYPE: DNA
<213> ORGANISM: Trichoderma reesei

<400> SEQUENCE: 1

```
atggcggtga atcgcatccg gggcgccttt gccgcgcctc ggaagggaga gacattcgag    60
ctgcgggccg gcctggtgtc gcagtatgcc tacgagcgga aggagtccat ccagaagacc   120
atcatggcca tgacgctggg caaggacgtg tccgccctgt tcccagacgt cttgaagaac   180
attgccacgt ccgacctgga ccagaagaag ctggtctacc tctacctcat gtatgtggct   240
gcagacaatg gccgaccatg atcacacaca cggagcgaag gacgagatac tgcctgacgt   300
ggcgatgcgg tgctaacgtg gagtgtgacc ccaggaacta cgcaaagaca cacccagacc   360
tctgcattct cgccgtcaac acgttcgtgc aagactcgga agacccgaac ccgctggtgc   420
gagcgctggc catccgcaca atgggctgca tccgggtgga caagatggtc gactacatgg   480
aggagccgct gcggaagacg ctgcgggacg agtcgccgta cgtgcgcaag acggccgcca   540
tctgcgtggc caagctgttc gacctgaacc cggccatgtg catcgagaac ggcttcatcg   600
agacgctgca ggagatgatt ggcgacccga accccatggt ggtcgcaaac tcggtccagg   660
cgctggccga gattagcgag acggcgcccg agacgcgggc gctgctggtg acgccccgg   720
tgctcaagaa gctgcttatg ccatgaacg aatgcaccga atggggtaga atcaccattc   780
tgaccgtgct ggcagactac gctgccaccg acgtcaagga gtcggagcac atctgcgaga   840
gggtcattcc gcagttccag cacgtcaacc ctagcgtggt cctggctgct gtcaaggtgg   900
tctttattca tatgaagtcg attaacccgg agctcgtgcg gtcatatctt aagaagatgg   960
cgcctccact cggtgcgttc cgatcatgtc cccgatttga catctgagaa gacatgacgt  1020
gactatgcta acactgcagc ttgtatacag tcacactggt tgcttctgcc ccgaggtcc   1080
aatacgtcgc tctcagaaac attgatctgc tccttcaagc caagcccgac atcctgagca  1140
aagagttaag agtcttcttt tgcaaataca cgacccgcc gtacgtcaag atgcaaaagc  1200
tggaaatcat ggtcaggata gcaaacgaaa agaactacga gcagctcctg tctgagctca  1260
aggaatacgc cctggaagtg gacatggact ttgtgcgccg agccatcaag gccatcggcc  1320
aggtggccat caagattgag gaggccagtg gcaagtgcgt gcaggcgctg aagatcttc   1380
tcgctaccaa ggtcaactac gtggtgcaag aggttgtcgt ggtcatcaaa gatatcctgc  1440
gaaagtaccc cggttacgag ggcgtgatcc cctcgctctg caactacatt gacgagctcg  1500
acgaggccaa tgctcgtgga tccctcatct ggattgtggg agagtacgcc gagaagatta  1560
gcaacgctga ggagattctg gagggtttg tagacacctt tttggaggag ttcactcagg  1620
tatgtggaga gctgtggaaa agtcgcggat tttggctaat cgaactgcag acacaactcc  1680
agatccttac agctgttgtt aagctgtttt tgaagaagcc gagtggcgcg cagggcctgg  1740
ttcagaaggt gctgcaggag gcaacaacca acaacgacaa ccccgatatc cgcgacagag  1800
catacgtcta ctggcgattg ttatcggag atttggaggt ggccaaggta ggagtcgttg  1860
gcgtcctttg atgagagctg cgcatactga cggatctcaa gaacattgtc ctgtcacaga  1920
agccgaccat ttcaacaaca atgacaagcc tgccgactgc gctactggag cagctgctgt  1980
cggagctgtc aactctggcg tcggtatacc acaagccccc ggaagccttt gtcggcaagg  2040
gccggttcgg tgccgacgag atccagcgag ccgccatcca ggagcagcgc cagaacgccg  2100
cggaaaaccc catcgccgca tccgtggctg ccgccgccgc caatggctcc tcgtcggtct  2160
cgcaaaacaa cattgagaac ctgctggaca ttgactttga cggcgcagca ccggcctctc  2220
aggagcagaa cagcgcggcg ggaacacctg accgggtgtc gagcccggcc acgggtggca  2280
tggccgacat gatgagcatg tttgatgcgc ctccggctgg cagctctgga ggtgctccgt  2340
```

-continued

```
ccggcggcat gaacgacttg atgaacggat ttgaggggct caactttggg gccacgagta    2400
caaatcagcc gttgccggcg gcgatgcagc tgcacaatgc gcaaggcggc tctcagccga    2460
agaaggatag cgatgatctt tgggtttgt tgtaaatgtt ggaggagcgt atatgcatgc     2520
aagcagcaag ccagaagggg agaagaatcg acaagagaga ctggaggagg aggcaaggga    2580
ggggggggg                                                           2589
```

<210> SEQ ID NO 2
<211> LENGTH: 735
<212> TYPE: PRT
<213> ORGANISM: Trichoderma reesei

<400> SEQUENCE: 2

Met Ala Val Asn Arg Ile Arg Gly Ala Phe Ala Ala Pro Arg Lys Gly
1               5                   10                  15

Glu Thr Phe Glu Leu Arg Ala Gly Leu Val Ser Gln Tyr Ala Tyr Glu
            20                  25                  30

Arg Lys Glu Ser Ile Gln Lys Thr Ile Met Ala Met Thr Leu Gly Lys
        35                  40                  45

Asp Val Ser Ala Leu Phe Pro Asp Val Leu Lys Asn Ile Ala Thr Ser
    50                  55                  60

Asp Leu Asp Gln Lys Lys Leu Val Tyr Leu Tyr Leu Met Asn Tyr Ala
65                  70                  75                  80

Lys Thr His Pro Asp Leu Cys Ile Leu Ala Val Asn Thr Phe Val Gln
                85                  90                  95

Asp Ser Glu Asp Pro Asn Pro Leu Val Arg Ala Leu Ala Ile Arg Thr
            100                 105                 110

Met Gly Cys Ile Arg Val Asp Lys Met Val Asp Tyr Met Glu Glu Pro
        115                 120                 125

Leu Arg Lys Thr Leu Arg Asp Glu Ser Pro Tyr Val Arg Lys Thr Ala
    130                 135                 140

Ala Ile Cys Val Ala Lys Leu Phe Asp Leu Asn Pro Ala Met Cys Ile
145                 150                 155                 160

Glu Asn Gly Phe Ile Glu Thr Leu Gln Glu Met Ile Gly Asp Pro Asn
                165                 170                 175

Pro Met Val Val Ala Asn Ser Val Gln Ala Leu Ala Glu Ile Ser Glu
            180                 185                 190

Thr Ala Pro Glu Thr Arg Ala Leu Leu Val Thr Pro Val Leu Lys
        195                 200                 205

Lys Leu Leu Met Ala Met Asn Glu Cys Thr Glu Trp Gly Arg Ile Thr
    210                 215                 220

Ile Leu Thr Val Leu Ala Asp Tyr Ala Ala Thr Asp Val Lys Glu Ser
225                 230                 235                 240

Glu His Ile Cys Glu Arg Val Ile Pro Gln Phe Gln His Val Asn Pro
                245                 250                 255

Ser Val Val Leu Ala Ala Val Lys Val Phe Ile His Met Lys Ser
            260                 265                 270

Ile Asn Pro Glu Leu Val Arg Ser Tyr Leu Lys Lys Met Ala Pro Pro
        275                 280                 285

Leu Val Thr Leu Val Ala Ser Ala Pro Glu Val Gln Tyr Val Ala Leu
    290                 295                 300

Arg Asn Ile Asp Leu Leu Leu Gln Ala Lys Pro Asp Ile Leu Ser Lys
305                 310                 315                 320

Glu Leu Arg Val Phe Phe Cys Lys Tyr Asn Asp Pro Pro Tyr Val Lys

```
            325                 330                 335
Met Gln Lys Leu Glu Ile Met Val Arg Ile Ala Asn Glu Lys Asn Tyr
            340                 345                 350
Glu Gln Leu Leu Ser Glu Leu Lys Glu Tyr Ala Leu Glu Val Asp Met
            355                 360                 365
Asp Phe Val Arg Arg Ala Ile Lys Ala Ile Gly Gln Val Ala Ile Lys
            370                 375                 380
Ile Glu Ala Ser Gly Lys Cys Val Gln Ala Leu Glu Asp Leu Leu
385                 390                 395                 400
Ala Thr Lys Val Asn Tyr Val Gln Glu Val Val Val Ile Lys
                    405                 410                 415
Asp Ile Leu Arg Lys Tyr Pro Gly Tyr Glu Gly Val Ile Pro Ser Leu
            420                 425                 430
Cys Asn Tyr Ile Asp Glu Leu Asp Glu Ala Asn Ala Arg Gly Ser Leu
            435                 440                 445
Ile Trp Ile Val Gly Glu Tyr Ala Glu Lys Ile Ser Asn Ala Glu Glu
            450                 455                 460
Ile Leu Glu Gly Phe Val Asp Thr Phe Leu Glu Glu Phe Thr Gln Thr
465                 470                 475                 480
Gln Leu Gln Ile Leu Thr Ala Val Val Lys Leu Phe Leu Lys Lys Pro
                    485                 490                 495
Ser Gly Ala Gln Gly Leu Val Gln Lys Val Leu Gln Glu Ala Thr Thr
            500                 505                 510
Asn Asn Asp Asn Pro Asp Ile Arg Asp Arg Ala Tyr Val Tyr Trp Arg
            515                 520                 525
Leu Leu Ser Gly Asp Leu Glu Val Ala Lys Asn Ile Val Leu Ser Gln
            530                 535                 540
Lys Pro Thr Ile Ser Thr Thr Met Thr Ser Leu Pro Thr Ala Leu Leu
545                 550                 555                 560
Glu Gln Leu Leu Ser Glu Leu Ser Thr Leu Ala Ser Val Tyr His Lys
            565                 570                 575
Pro Pro Glu Ala Phe Val Gly Lys Gly Arg Phe Gly Ala Asp Glu Ile
            580                 585                 590
Gln Arg Ala Ala Ile Gln Glu Gln Arg Gln Asn Ala Ala Glu Asn Pro
            595                 600                 605
Ile Ala Ala Ser Val Ala Ala Ala Ala Asn Gly Ser Ser Ser Val
            610                 615                 620
Ser Gln Asn Asn Ile Glu Asn Leu Leu Asp Ile Asp Phe Asp Gly Ala
625                 630                 635                 640
Ala Pro Ala Ser Gln Glu Gln Asn Ser Ala Ala Gly Thr Pro Asp Arg
            645                 650                 655
Val Ser Ser Pro Ala Thr Gly Gly Met Ala Asp Met Met Ser Met Phe
            660                 665                 670
Asp Ala Pro Pro Ala Gly Ser Ser Gly Gly Ala Pro Ser Gly Gly Met
            675                 680                 685
Asn Asp Leu Met Asn Gly Phe Glu Gly Leu Asn Phe Gly Ala Thr Ser
            690                 695                 700
Thr Asn Gln Pro Leu Pro Ala Ala Met Gln Leu His Asn Ala Gln Gly
705                 710                 715                 720
Gly Ser Gln Pro Lys Lys Asp Ser Asp Asp Leu Leu Gly Leu Leu
                    725                 730                 735
```

<210> SEQ ID NO 3

```
<211> LENGTH: 735
<212> TYPE: PRT
<213> ORGANISM: Trichoderma citrinoviride

<400> SEQUENCE: 3
```

| | | | | | | | | | | | | | | |
|---|---|---|---|---|---|---|---|---|---|---|---|---|---|---|
| Met | Ala | Val | Asn | Arg | Ile | Arg | Gly | Ala | Phe | Ala | Ala | Pro | Arg | Lys | Gly |
| 1 | | | | 5 | | | | | 10 | | | | | 15 | |

Glu Thr Phe Glu Leu Arg Ala Gly Leu Val Ser Gln Tyr Ala Tyr Glu
                20                   25                   30

Arg Lys Glu Ser Ile Gln Lys Thr Ile Met Ala Met Thr Leu Gly Lys
            35                   40                   45

Asp Val Ser Ala Leu Phe Pro Asp Val Leu Lys Asn Ile Ala Thr Ser
50                       55                       60

Asp Leu Asp Gln Lys Lys Leu Val Tyr Leu Tyr Leu Met Asn Tyr Ala
65                       70                       75                       80

Lys Thr His Pro Asp Leu Cys Ile Leu Ala Val Asn Thr Phe Val Gln
                    85                   90                   95

Asp Ser Glu Asp Pro Asn Pro Leu Val Arg Ala Leu Ala Ile Arg Thr
                100                 105                 110

Met Gly Cys Ile Arg Val Asp Lys Met Val Asp Tyr Met Glu Glu Pro
            115                 120                 125

Leu Arg Lys Thr Leu Arg Asp Glu Ser Pro Tyr Val Arg Lys Thr Ala
        130                 135                 140

Ala Ile Cys Val Ala Lys Leu Phe Asp Leu Asn Pro Ala Met Cys Ile
145                 150                 155                 160

Glu Asn Gly Phe Ile Glu Thr Leu Gln Glu Met Ile Gly Asp Pro Asn
                165                 170                 175

Pro Met Val Val Ala Asn Ser Val Gln Ala Leu Ala Glu Ile Ser Glu
            180                 185                 190

Thr Ala Pro Glu Thr Arg Ala Leu Leu Val Thr Pro Val Leu Lys
        195                 200                 205

Lys Leu Leu Met Ala Met Asn Glu Cys Thr Glu Trp Gly Arg Ile Thr
210                 215                 220

Ile Leu Thr Val Leu Ala Asp Tyr Ala Ala Thr Asp Val Lys Glu Ser
225                 230                 235                 240

Glu His Ile Cys Glu Arg Val Ile Pro Gln Phe Gln His Val Asn Pro
                245                 250                 255

Ser Val Val Leu Ala Ala Val Lys Val Val Phe Ile His Met Lys Ser
            260                 265                 270

Ile Asn Pro Glu Leu Val Arg Ser Tyr Leu Lys Lys Met Ala Pro Pro
        275                 280                 285

Leu Val Thr Leu Val Ala Ser Ala Pro Glu Val Gln Tyr Val Ala Leu
        290                 295                 300

Arg Asn Ile Asp Leu Leu Leu Gln Ala Lys Pro Asp Ile Leu Ser Lys
305                 310                 315                 320

Glu Leu Arg Val Phe Phe Cys Lys Tyr Asn Asp Pro Pro Tyr Val Lys
                325                 330                 335

Met Gln Lys Leu Glu Ile Met Val Arg Ile Ala Asn Glu Lys Asn Tyr
            340                 345                 350

Glu Gln Leu Leu Ser Glu Leu Lys Glu Tyr Ala Leu Glu Val Asp Met
        355                 360                 365

Asp Phe Val Arg Arg Ala Ile Lys Ala Ile Gly Gln Val Ala Ile Lys
    370                 375                 380

Ile Glu Asp Ala Ser Ala Lys Cys Val Gln Ala Leu Glu Asp Leu Leu

```
                385                 390                 395                 400
        Ala Thr Lys Val Asn Tyr Val Gln Glu Val Val Val Ile Lys
                        405                 410                 415

Asp Ile Leu Arg Lys Tyr Pro Gly Tyr Glu Gly Val Ile Pro Ser Leu
                        420                 425                 430

Cys Asn Tyr Ile Asp Glu Leu Asp Glu Ala Asn Ala Arg Gly Ser Leu
                        435                 440                 445

Ile Trp Ile Val Gly Glu Tyr Ala Glu Lys Ile Ser Asn Ala Glu Glu
                        450                 455                 460

Ile Leu Glu Gly Phe Val Asp Thr Phe Leu Glu Glu Phe Thr Gln Thr
        465                 470                 475                 480

Gln Leu Gln Ile Leu Thr Ala Val Val Lys Leu Phe Leu Lys Lys Pro
                        485                 490                 495

Ser Gly Ala Gln Gly Leu Val Gln Lys Val Leu Gln Glu Ala Thr Thr
                        500                 505                 510

Asn Asn Asp Asn Pro Asp Ile Arg Asp Arg Ala Tyr Val Tyr Trp Arg
                        515                 520                 525

Leu Leu Ser Gly Asp Leu Glu Val Ala Lys Ser Ile Val Leu Ser Gln
                        530                 535                 540

Lys Pro Thr Ile Ser Thr Thr Met Thr Ser Leu Pro Ala Thr Leu Leu
        545                 550                 555                 560

Glu Gln Leu Leu Ser Glu Leu Ser Thr Leu Ala Ser Val Tyr His Lys
                        565                 570                 575

Pro Pro Glu Ala Phe Val Gly Lys Gly Arg Phe Gly Ala Asp Glu Ile
                        580                 585                 590

Gln Arg Ala Ala Ile Gln Glu Gln Arg Gln Asn Ala Ala Glu Asn Pro
                        595                 600                 605

Ile Ala Ala Ser Val Ala Ala Ala Ala Asn Gly Ser Ser Ser Val
                        610                 615                 620

Ser Gln Asn Asn Ile Glu Asn Leu Leu Asp Ile Asp Phe Asp Gly Ala
        625                 630                 635                 640

Ala Pro Ala Ser Gln Glu Gln Asn Ser Ala Ala Gly Thr Pro Asp Arg
                        645                 650                 655

Val Ser Ser Pro Ala Thr Gly Gly Met Ala Asp Met Met Ser Met Phe
                        660                 665                 670

Asp Ala Pro Pro Ala Gly Ser Ser Gly Gly Ala Pro Ser Gly Gly Met
                        675                 680                 685

Asn Asp Leu Met Asn Gly Phe Glu Gly Leu Asn Phe Gly Ala Thr Thr
                        690                 695                 700

Ala Asn Gln Pro Leu Pro Ala Ala Met Gln Leu His Asn Ala Gln Gly
        705                 710                 715                 720

Gly Ser Gln Pro Lys Lys Asp Ser Asp Asp Leu Leu Gly Leu Leu
                        725                 730                 735

<210> SEQ ID NO 4
<211> LENGTH: 734
<212> TYPE: PRT
<213> ORGANISM: Trichoderma longibrachiatum

<400> SEQUENCE: 4

Met Ala Val Asn Arg Ile Arg Gly Ala Phe Ala Ala Pro Arg Lys Gly
1               5                   10                  15

Glu Thr Phe Glu Leu Arg Ala Gly Leu Val Ser Gln Tyr Ala Tyr Glu
                20                  25                  30
```

```
Arg Lys Glu Ser Ile Gln Lys Thr Ile Met Ala Met Thr Leu Gly Lys
         35                  40                  45

Asp Val Ser Ala Leu Phe Pro Asp Val Leu Lys Asn Ile Ala Thr Ser
     50                  55                  60

Asp Leu Asp Gln Lys Lys Leu Val Tyr Leu Tyr Leu Met Asn Tyr Ala
 65                  70                  75                  80

Lys Thr His Pro Asp Leu Cys Ile Leu Ala Val Asn Thr Phe Val Gln
             85                  90                  95

Asp Ser Glu Asp Pro Asn Pro Leu Val Arg Ala Leu Ala Ile Arg Thr
             100                 105                 110

Met Gly Cys Ile Arg Val Asp Lys Met Val Asp Tyr Met Glu Glu Pro
             115                 120                 125

Leu Arg Lys Thr Leu Arg Asp Glu Ser Pro Tyr Val Arg Lys Thr Ala
         130                 135                 140

Ala Ile Cys Val Ala Lys Leu Phe Asp Leu Asn Pro Ala Met Cys Ile
145                 150                 155                 160

Glu Asn Gly Phe Ile Glu Ser Leu Gln Glu Met Ile Gly Asp Pro Asn
                 165                 170                 175

Pro Met Val Val Ala Asn Ser Val Gln Ala Leu Ala Glu Ile Ser Glu
             180                 185                 190

Thr Ala Pro Glu Thr Arg Ala Leu Leu Val Thr Pro Val Leu Lys
         195                 200                 205

Lys Leu Leu Met Ala Met Asn Glu Cys Thr Glu Trp Gly Arg Ile Thr
         210                 215                 220

Ile Leu Thr Val Leu Ala Asp Tyr Ala Ala Thr Asp Val Lys Glu Ser
225                 230                 235                 240

Glu His Ile Cys Glu Arg Val Ile Pro Gln Phe Gln His Val Asn Pro
                 245                 250                 255

Ser Val Val Leu Ala Ala Val Lys Val Phe Ile His Met Lys Ser
             260                 265                 270

Ile Asn Pro Glu Leu Val Arg Ser Tyr Leu Lys Lys Met Ala Pro Pro
         275                 280                 285

Leu Val Thr Leu Val Ala Ser Ala Pro Glu Val Gln Tyr Val Ala Leu
         290                 295                 300

Arg Asn Ile Asp Leu Leu Leu Gln Ala Lys Pro Asp Ile Leu Ser Lys
305                 310                 315                 320

Glu Leu Arg Val Phe Phe Cys Lys Tyr Asn Asp Pro Tyr Val Lys
                 325                 330                 335

Met Gln Lys Leu Glu Ile Met Val Arg Ile Ala Asn Glu Lys Asn Tyr
         340                 345                 350

Glu Gln Leu Leu Ser Glu Leu Lys Glu Tyr Ala Leu Glu Val Asp Met
         355                 360                 365

Asp Phe Val Arg Arg Ala Ile Lys Ala Ile Gly Gln Val Ala Ile Lys
 370                 375                 380

Ile Glu Glu Ala Ser Gly Lys Cys Val Gln Ala Leu Glu Asp Leu Leu
385                 390                 395                 400

Ala Thr Lys Val Asn Tyr Val Val Gln Glu Val Val Val Ile Lys
                 405                 410                 415

Asp Ile Leu Arg Lys Tyr Pro Gly Tyr Glu Gly Val Ile Pro Ser Leu
             420                 425                 430

Cys Asn Tyr Ile Asp Glu Leu Asp Glu Ala Asn Ala Arg Gly Ser Leu
             435                 440                 445

Ile Trp Ile Val Gly Glu Tyr Ala Glu Lys Ile Ser Asn Ala Glu Glu
```

```
            450                 455                 460
Ile Leu Glu Gly Phe Val Asp Thr Phe Leu Glu Glu Phe Thr Gln Thr
465                 470                 475                 480

Gln Leu Gln Ile Leu Thr Ala Val Val Lys Leu Phe Leu Lys Lys Pro
                485                 490                 495

Ser Gly Ala Gln Gly Leu Val Gln Lys Val Leu Gln Glu Ala Thr Thr
                500                 505                 510

Asn Asn Asp Asn Pro Asp Ile Arg Asp Arg Ala Tyr Val Tyr Trp Arg
                515                 520                 525

Leu Leu Ser Gly Asp Leu Glu Val Ala Lys Thr Ile Val Leu Ser Gln
                530                 535                 540

Lys Pro Thr Ile Ser Thr Thr Met Thr Ser Leu Pro Ala Ala Leu Leu
545                 550                 555                 560

Glu Gln Leu Leu Ser Glu Leu Ser Thr Leu Ala Ser Val Tyr His Lys
                565                 570                 575

Pro Pro Glu Ala Phe Val Gly Lys Gly Arg Phe Gly Ala Asp Glu Ile
                580                 585                 590

Gln Arg Ala Ala Ile Gln Glu Gln Arg Gln Asn Ala Ala Glu Asn Pro
                595                 600                 605

Ile Ala Ala Ser Val Ala Ala Ala Asn Gly Ser Ser Val Ser Gln
610                 615                 620

Asn Asn Ile Glu Asn Leu Leu Asp Ile Asp Phe Asp Gly Ala Ala Pro
625                 630                 635                 640

Ala Ser Gln Glu Gln Asn Ser Ala Ala Gly Thr Pro Asp Arg Val Ser
                645                 650                 655

Ser Pro Ala Thr Gly Gly Met Ala Asp Met Met Ser Met Phe Asp Ala
                660                 665                 670

Pro Pro Ala Gly Ser Ser Gly Gly Ala Pro Ser Gly Gly Met Asn Asp
                675                 680                 685

Leu Met Asn Gly Phe Glu Gly Leu Asn Phe Gly Ala Thr Ser Thr Asn
                690                 695                 700

Gln Pro Leu Pro Ala Ala Met Gln Leu His Asn Ala Gln Gly Gly Gly
705                 710                 715                 720

Ser Gln Pro Asn Lys Asp Ser Asp Asp Leu Leu Gly Leu Leu
                725                 730

<210> SEQ ID NO 5
<211> LENGTH: 732
<212> TYPE: PRT
<213> ORGANISM: Trichoderma virens

<400> SEQUENCE: 5

Met Ala Val Asn Arg Ile Arg Gly Ala Phe Ala Ala Pro Arg Lys Gly
1               5                   10                  15

Glu Thr Phe Glu Leu Arg Ala Gly Leu Val Ser Gln Tyr Ala Tyr Glu
                20                  25                  30

Arg Lys Glu Ser Ile Gln Lys Thr Ile Met Ala Met Thr Leu Gly Lys
                35                  40                  45

Asp Val Ser Ala Leu Phe Pro Asp Val Leu Lys Asn Ile Ala Thr Ala
                50                  55                  60

Asp Leu Asp Gln Lys Lys Leu Val Tyr Leu Tyr Leu Met Asn Tyr Ala
65                  70                  75                  80

Lys Thr His Pro Asp Leu Cys Ile Leu Ala Val Asn Thr Phe Val Gln
                85                  90                  95
```

```
Asp Ser Glu Asp Pro Asn Pro Leu Val Arg Ala Leu Ala Ile Arg Thr
                100                 105                 110

Met Gly Cys Ile Arg Val Asp Lys Met Val Asp Tyr Met Glu Glu Pro
            115                 120                 125

Leu Arg Lys Thr Leu Arg Asp Glu Ser Pro Tyr Val Arg Lys Thr Ala
        130                 135                 140

Ala Ile Cys Val Ala Lys Leu Phe Asp Leu Asn Pro Ala Met Cys Ile
145                 150                 155                 160

Glu Asn Gly Phe Ile Glu Thr Leu Gln Glu Met Ile Gly Asp Pro Asn
                165                 170                 175

Pro Met Val Val Ala Asn Ser Val Gln Ala Leu Ala Glu Ile Ser Glu
            180                 185                 190

Thr Ala Pro Glu Thr Arg Ala Leu Leu Val Thr Pro Ala Val Leu Lys
        195                 200                 205

Lys Leu Leu Met Ala Met Asn Glu Cys Thr Glu Trp Gly Arg Ile Thr
210                 215                 220

Ile Leu Thr Val Leu Ala Asp Tyr Ile Ala Asp Val Lys Glu Ser
225                 230                 235                 240

Glu His Ile Cys Glu Arg Val Ile Pro Gln Phe Gln His Val Asn Pro
                245                 250                 255

Ser Val Val Leu Ala Ala Val Lys Val Phe Ile His Met Lys Ser
            260                 265                 270

Ile Ser Pro Glu Leu Val Arg Ser Tyr Leu Lys Lys Met Ala Pro Pro
        275                 280                 285

Leu Val Thr Leu Val Ala Ser Ala Pro Glu Val Gln Tyr Val Ala Leu
            290                 295                 300

Arg Asn Ile Asp Leu Leu Leu Gln Ala Lys Pro Asp Ile Leu Ser Lys
305                 310                 315                 320

Glu Leu Arg Val Phe Phe Cys Lys Tyr Asn Asp Pro Tyr Val Lys
                325                 330                 335

Met Gln Lys Leu Glu Ile Met Val Arg Ile Ala Asn Glu Lys Asn Tyr
            340                 345                 350

Glu Gln Leu Leu Ser Glu Leu Lys Glu Tyr Ala Leu Glu Val Asp Met
        355                 360                 365

Asp Phe Val Arg Arg Ala Ile Lys Ala Ile Gly Gln Val Ala Ile Lys
    370                 375                 380

Ile Glu Asp Ala Ser Ala Lys Cys Val Gln Ala Leu Glu Asp Leu Leu
385                 390                 395                 400

Ala Thr Lys Val Asn Tyr Val Val Gln Glu Val Val Val Ile Lys
            405                 410                 415

Asp Ile Leu Arg Lys Tyr Pro Gly Tyr Glu Gly Val Ile Pro Ser Leu
        420                 425                 430

Cys Asn Tyr Ile Asp Glu Leu Asp Glu Ala Asn Ala Arg Gly Ser Leu
            435                 440                 445

Ile Trp Ile Val Gly Glu Tyr Ala Glu Lys Ile Ser Asn Ala Glu Glu
    450                 455                 460

Ile Leu Glu Gly Phe Val Asp Thr Phe Ser Glu Glu Phe Thr Gln Thr
465                 470                 475                 480

Gln Leu Gln Ile Leu Thr Ala Val Val Lys Leu Phe Leu Lys Lys Pro
            485                 490                 495

Ser Gly Ala Gln Ser Leu Val Gln Lys Val Leu Gln Glu Ala Thr Thr
        500                 505                 510

Asn Asn Asp Asn Pro Asp Ile Arg Asp Arg Ala Tyr Val Tyr Trp Arg
```

```
                515                 520                 525

Leu Leu Ser Gly Asp Leu Glu Val Ala Lys Ser Ile Val Leu Ser Gln
            530                 535                 540

Lys Pro Thr Ile Ser Thr Thr Met Thr Ser Leu Pro Ala Thr Leu Leu
545                 550                 555                 560

Glu Gln Leu Leu Ser Glu Leu Ser Thr Leu Ala Ser Val Tyr His Lys
                565                 570                 575

Pro Pro Glu Ala Phe Val Gly Lys Gly Arg Phe Gly Ala Asp Glu Ile
            580                 585                 590

Gln Arg Ala Ala Ile Gln Glu Gln Arg Gln Asn Ala Ala Glu Asn Pro
                595                 600                 605

Ile Ala Ala Ser Val Ala Ala Ala Ala Asn Gly Ser Ala Ser Ser
            610                 615                 620

Gln Ser Asn Ile Glu Asn Leu Leu Asp Ile Asp Phe Asp Gly Ala Ala
625                 630                 635                 640

Pro Ala Ser Gln Glu Gln Ala Ser Ala Ala Gly Thr Pro Asp Arg Val
                645                 650                 655

Ser Ser Pro Ala Thr Gly Gly Met Ala Asp Met Met Ser Met Phe Asp
            660                 665                 670

Ala Pro Ala Ala Ser Gly Ser Ser Ala Pro Ala Gly Gly Met
                675                 680                 685

Asn Asp Leu Met Asn Gly Phe Glu Gly Leu Asn Phe Gly Ala Ala Asn
690                 695                 700

Ala Ser Gln Pro Leu Pro Ala Ala Met Gln Leu His Gly Gly Ser Glu
705                 710                 715                 720

Pro Lys Lys Asp Ser Asp Asp Leu Leu Gly Leu Leu
                725                 730

<210> SEQ ID NO 6
<211> LENGTH: 735
<212> TYPE: PRT
<213> ORGANISM: Trichoderma atroviride

<400> SEQUENCE: 6

Met Ala Val Asn Arg Ile Arg Gly Ala Phe Ala Ala Pro Arg Lys Gly
1               5                   10                  15

Glu Thr Phe Glu Leu Arg Ala Gly Leu Val Ser Gln Tyr Ala Tyr Glu
                20                  25                  30

Arg Lys Glu Ser Ile Gln Lys Thr Ile Met Ala Met Thr Leu Gly Lys
            35                  40                  45

Asp Val Ser Ala Leu Phe Pro Asp Val Leu Lys Asn Ile Ala Thr Gly
50                  55                  60

Asp Leu Asp Gln Lys Lys Leu Val Tyr Leu Tyr Leu Met Asn Tyr Ala
65                  70                  75                  80

Lys Thr His Pro Asp Leu Cys Ile Leu Ala Val Asn Thr Phe Val Gln
                85                  90                  95

Asp Ser Glu Asp Pro Asn Pro Leu Val Arg Ala Leu Ala Ile Arg Thr
            100                 105                 110

Met Gly Cys Ile Arg Val Asp Lys Met Val Asp Tyr Met Glu Glu Pro
        115                 120                 125

Leu Arg Lys Thr Leu Arg Asp Glu Ser Pro Tyr Val Arg Lys Thr Ala
        130                 135                 140

Ala Ile Cys Val Ala Lys Leu Phe Asp Leu Asn Pro Ala Leu Cys Ile
145                 150                 155                 160
```

```
Glu Asn Gly Phe Ile Asp Ser Leu Gln Glu Met Ile Gly Asp Pro Asn
                165                 170                 175
Pro Met Val Val Ala Asn Ser Val Gln Ala Leu Ala Glu Ile Ser Glu
            180                 185                 190
Thr Ala Pro Glu Thr Arg Ala Leu Leu Val Thr Pro Pro Ile Leu Lys
        195                 200                 205
Lys Leu Leu Met Ala Met Asn Glu Cys Thr Glu Trp Gly Arg Ile Thr
    210                 215                 220
Ile Leu Thr Val Leu Ala Asp Tyr Val Ala Asp Val Lys Glu Ser
225                 230                 235                 240
Glu His Ile Cys Glu Arg Val Ile Pro Gln Phe Gln His Val Asn Pro
                245                 250                 255
Ser Val Val Leu Ala Ala Val Lys Val Val Phe Ile His Met Lys Ala
            260                 265                 270
Ile Asn Ser Glu Leu Val Arg Ser Tyr Leu Lys Lys Met Ala Pro Pro
        275                 280                 285
Leu Val Thr Leu Val Ala Ser Gln Pro Glu Val Gln Tyr Val Ala Leu
    290                 295                 300
Arg Asn Ile Asp Leu Leu Leu Gln Ala Lys Pro Asp Ile Leu Ser Lys
305                 310                 315                 320
Glu Leu Arg Val Phe Phe Cys Lys Tyr Asn Asp Pro Pro Tyr Val Lys
                325                 330                 335
Met Gln Lys Leu Glu Ile Met Val Arg Ile Ala Asn Glu Lys Asn Tyr
            340                 345                 350
Glu Gln Leu Leu Ala Glu Leu Lys Glu Tyr Ala Leu Glu Val Asp Met
        355                 360                 365
Asp Phe Val Arg Arg Ala Ile Lys Ala Ile Gly Gln Val Ala Ile Lys
    370                 375                 380
Ile Glu Asp Ala Ser Ala Lys Cys Val Gln Ala Leu Glu Asp Leu Leu
385                 390                 395                 400
Ala Thr Lys Ala Asn Tyr Val Val Gln Glu Val Val Val Ile Lys
                405                 410                 415
Asp Ile Leu Arg Lys Tyr Pro Gly Tyr Glu Gly Val Ile Pro Ser Leu
            420                 425                 430
Cys Asn Tyr Ile Asp Glu Leu Asp Glu Ala Asp Ala Arg Gly Ser Leu
        435                 440                 445
Ile Trp Ile Val Gly Glu Tyr Ala Glu Lys Ile Ser Asn Ala Glu Glu
    450                 455                 460
Ile Leu Asp Gly Phe Val Asp Thr Phe Ser Glu Glu Phe Thr Gln Thr
465                 470                 475                 480
Gln Leu Gln Ile Leu Thr Ala Val Val Lys Leu Phe Leu Lys Lys Pro
                485                 490                 495
Ser Gly Ala Gln Ser Leu Val Gln Lys Val Leu Gln Glu Ala Thr Thr
            500                 505                 510
Asn Asn Asp Asn Pro Asp Ile Arg Asp Arg Ala Tyr Val Tyr Trp Arg
        515                 520                 525
Leu Leu Ser Gly Asp Leu Glu Val Ala Lys Asn Ile Val Leu Ser Thr
    530                 535                 540
Arg Pro Thr Ile Ser Thr Thr Met Thr Ser Leu Pro Thr Thr Leu Leu
545                 550                 555                 560
Glu Gln Leu Leu Ser Glu Leu Ser Thr Leu Ala Ser Val Tyr His Lys
                565                 570                 575
Pro Pro Glu Ala Phe Val Gly Lys Gly Arg Phe Gly Ala Asp Glu Ile
```

```
                    580                 585                 590
Gln Arg Ala Ala Ile Gln Glu Gln Arg Gln Asn Ala Ala Glu Asn Pro
            595                 600                 605

Ile Ala Ala Ser Val Ala Ala Asn Gly Ser Gly Ser Val Ser Gln Asn
        610                 615                 620

Asn Ile Glu Asn Leu Leu Asp Ile Asp Phe Asp Gly Ala Ala Pro Ala
625                 630                 635                 640

Ser His Glu Gln Asn Ser Ala Thr Gly Thr Pro Asp Arg Val Gln Ser
                645                 650                 655

Pro Ala Thr Ser Gly Met Ala Asp Met Met Ser Met Phe Asp Ala Pro
            660                 665                 670

Pro Ala Gly Gly Ser Ser Ala Pro Ala Ala Pro Ala Gly Gly Met
        675                 680                 685

Asn Asp Leu Met Asn Gly Phe Glu Gly Leu Asn Phe Gly Gly Ala Thr
        690                 695                 700

Thr Ser Glu Pro Leu Pro Ala Ala Met Gln Leu His Asn Ala His Gly
705                 710                 715                 720

Gly Ala Gln Pro Lys Lys Asp Ser Asp Asp Leu Leu Gly Leu Leu
                725                 730                 735

<210> SEQ ID NO 7
<211> LENGTH: 735
<212> TYPE: PRT
<213> ORGANISM: Trichoderma gamsii

<400> SEQUENCE: 7

Met Ala Val Asn Arg Ile Arg Gly Ala Phe Ala Ala Pro Arg Lys Gly
1               5                   10                  15

Glu Thr Phe Glu Leu Arg Ala Gly Leu Val Ser Gln Tyr Ala Tyr Glu
            20                  25                  30

Arg Lys Glu Ser Ile Gln Lys Thr Ile Met Ala Met Thr Leu Gly Lys
        35                  40                  45

Asp Val Ser Ala Leu Phe Pro Asp Val Leu Lys Asn Ile Ala Thr Gly
    50                  55                  60

Asp Leu Asp Gln Lys Lys Leu Val Tyr Leu Tyr Leu Met Asn Tyr Ala
65                  70                  75                  80

Lys Thr His Pro Asp Leu Cys Ile Leu Ala Val Asn Thr Phe Val Gln
                85                  90                  95

Asp Ser Glu Asp Pro Asn Pro Leu Val Arg Ala Leu Ala Ile Arg Thr
            100                 105                 110

Met Gly Cys Ile Arg Val Asp Lys Met Val Asp Tyr Met Glu Glu Pro
        115                 120                 125

Leu Arg Lys Thr Leu Arg Asp Glu Ser Pro Tyr Val Arg Lys Thr Ala
    130                 135                 140

Ala Ile Cys Val Ala Lys Leu Phe Asp Leu Asn Pro Ala Leu Cys Ile
145                 150                 155                 160

Glu Asn Gly Phe Ile Asp Ser Leu Gln Glu Met Ile Gly Asp Pro Asn
                165                 170                 175

Pro Met Val Val Ala Asn Ser Val Gln Ala Leu Ala Glu Ile Ser Glu
            180                 185                 190

Thr Ala Pro Glu Thr Arg Ala Leu Leu Val Thr Pro Ile Leu Lys
        195                 200                 205

Lys Leu Leu Met Ala Met Asn Glu Cys Thr Glu Trp Gly Arg Ile Thr
    210                 215                 220
```

```
Ile Leu Thr Val Leu Ala Asp Tyr Val Ala Asp Val Lys Glu Ser
225                 230                 235                 240

Glu His Ile Cys Glu Arg Val Ile Pro Gln Phe Gln His Val Asn Pro
                245                 250                 255

Ser Val Leu Ala Ala Val Lys Val Phe Ile His Met Lys Ala
260                 265                 270

Ile Asn Ser Glu Leu Val Arg Ser Tyr Leu Lys Lys Met Ala Pro Pro
            275                 280                 285

Leu Val Thr Leu Val Ala Ser Gln Pro Glu Val Gln Tyr Val Ala Leu
        290                 295                 300

Arg Asn Ile Asp Leu Leu Gln Ala Lys Pro Asp Ile Leu Ser Lys
305                 310                 315                 320

Glu Leu Arg Val Phe Phe Cys Lys Tyr Asn Asp Pro Pro Tyr Val Lys
                325                 330                 335

Met Gln Lys Leu Glu Ile Met Val Arg Ile Ala Asn Glu Lys Asn Tyr
            340                 345                 350

Glu Gln Leu Leu Ala Glu Leu Lys Glu Tyr Ala Leu Glu Val Asp Met
        355                 360                 365

Asp Phe Val Arg Arg Ala Ile Lys Ala Ile Gly Gln Val Ala Ile Lys
    370                 375                 380

Ile Glu Glu Ser Ser Ala Lys Cys Val Gln Ala Leu Glu Asp Leu Leu
385                 390                 395                 400

Ala Thr Lys Val Asn Tyr Val Gln Glu Val Val Val Ile Lys
                405                 410                 415

Asp Ile Leu Arg Lys Tyr Pro Gly Tyr Glu Gly Val Ile Pro Ser Leu
            420                 425                 430

Cys Asp Tyr Ile Asp Glu Leu Asp Glu Ala Asn Ala Arg Gly Ser Leu
        435                 440                 445

Ile Trp Ile Val Gly Glu Tyr Ala Glu Lys Ile Ser Asn Ala Glu Glu
    450                 455                 460

Ile Leu Asp Gly Phe Val Asp Thr Phe Ser Glu Phe Thr Gln Thr
465                 470                 475                 480

Gln Leu Gln Ile Leu Thr Ala Val Val Lys Leu Phe Leu Lys Lys Pro
                485                 490                 495

Ser Gly Ala Gln Ser Leu Val Gln Lys Val Leu Gln Glu Ala Thr Thr
            500                 505                 510

Asn Asn Asp Asn Pro Asp Ile Arg Asp Arg Ala Tyr Val Tyr Trp Arg
        515                 520                 525

Leu Leu Ser Gly Asp Leu Glu Val Ala Lys Asn Ile Val Leu Ser Thr
    530                 535                 540

Lys Pro Thr Ile Ser Thr Thr Met Thr Ser Leu Pro Thr Ser Leu Leu
545                 550                 555                 560

Glu Gln Leu Leu Ser Glu Leu Ser Thr Leu Ala Ser Val Tyr His Lys
                565                 570                 575

Pro Pro Glu Ala Phe Val Gly Lys Gly Arg Phe Gly Ala Asp Glu Ile
            580                 585                 590

Gln Arg Ala Ala Ile Gln Glu Gln Arg Gln Asn Ala Ala Glu Asn Pro
        595                 600                 605

Ile Ala Val Ser Val Ala Ala Asn Gly Ser Gly Ser Val Ser Gln Asn
    610                 615                 620

Asn Ile Glu Asn Leu Leu Asp Ile Asp Phe Asp Gly Ala Ala Pro Ala
625                 630                 635                 640

Ser His Glu Gln Asn Ser Ala Thr Gly Thr Pro Asp Arg Val Gln Ser
```

```
                  645                 650                 655
Pro Ala Thr Gly Gly Met Ala Asp Met Met Ser Met Phe Asp Ala Pro
                660                 665                 670

Pro Ala Gly Gly Ser Ala Ala Pro Ala Ala Pro Ala Gly Gly Met
            675                 680                 685

Asn Asp Leu Met Asn Gly Phe Glu Gly Leu Asn Phe Gly Gly Ala Thr
            690                 695                 700

Asn Ser Glu Pro Leu Pro Ala Ala Met Gln Leu His Asn Ala Gln Gly
705                 710                 715                 720

Gly Thr Gln Pro Lys Lys Asp Ser Asp Leu Leu Gly Leu Leu
                725                 730                 735

<210> SEQ ID NO 8
<211> LENGTH: 735
<212> TYPE: PRT
<213> ORGANISM: Trichoderma asperellum

<400> SEQUENCE: 8

Met Ala Val Asn Arg Ile Arg Gly Ala Phe Ala Ala Pro Arg Lys Gly
1               5                   10                  15

Glu Thr Phe Glu Leu Arg Ala Gly Leu Val Ser Gln Tyr Ala Tyr Glu
            20                  25                  30

Arg Lys Glu Ser Ile Gln Lys Thr Ile Met Ala Met Thr Leu Gly Lys
        35                  40                  45

Asp Val Ser Ala Leu Phe Pro Asp Val Leu Lys Asn Ile Ala Thr Gly
    50                  55                  60

Asp Leu Asp Gln Lys Lys Leu Val Tyr Leu Tyr Leu Met Asn Tyr Ala
65                  70                  75                  80

Lys Thr His Pro Asp Leu Cys Ile Leu Ala Val Asn Thr Phe Val Gln
                85                  90                  95

Asp Ser Glu Asp Pro Asn Pro Leu Val Arg Ala Leu Ala Ile Arg Thr
            100                 105                 110

Met Gly Cys Ile Arg Val Asp Lys Met Val Asp Tyr Met Glu Glu Pro
        115                 120                 125

Leu Arg Lys Thr Leu Arg Asp Glu Ser Pro Tyr Val Arg Lys Thr Ala
    130                 135                 140

Ala Ile Cys Val Ala Lys Leu Phe Asp Leu Asn Pro Ala Leu Cys Ile
145                 150                 155                 160

Glu Asn Gly Phe Ile Asp Ser Leu Gln Glu Met Ile Gly Asp Pro Asn
                165                 170                 175

Pro Met Val Val Ala Asn Ser Val Gln Ala Leu Ala Glu Ile Ser Glu
            180                 185                 190

Thr Ala Pro Glu Thr Arg Ala Leu Leu Val Thr Pro Ile Leu Lys
        195                 200                 205

Lys Leu Leu Met Ala Met Asn Glu Cys Thr Glu Trp Gly Arg Ile Thr
    210                 215                 220

Ile Leu Thr Val Leu Ala Asp Tyr Ala Ala Asp Val Lys Glu Ser
225                 230                 235                 240

Glu His Ile Cys Glu Arg Val Ile Pro Gln Phe Gln His Val Asn Pro
                245                 250                 255

Ser Val Val Leu Ala Ala Val Lys Val Phe Ile His Met Lys Ser
            260                 265                 270

Ile Asn Ser Glu Leu Val Arg Ser Tyr Leu Lys Lys Met Ala Pro Pro
        275                 280                 285
```

```
Leu Val Thr Leu Val Ala Ser Gln Pro Glu Val Gln Tyr Val Ala Leu
            290                 295                 300

Arg Asn Ile Asp Leu Leu Gln Ala Lys Pro Asp Ile Leu Ser Lys
305                 310                 315                 320

Glu Leu Arg Val Phe Phe Cys Lys Tyr Asn Asp Pro Pro Tyr Val Lys
                    325                 330                 335

Met Gln Lys Leu Glu Ile Met Val Arg Ile Ala Asn Glu Lys Asn Tyr
                340                 345                 350

Glu Gln Leu Leu Ala Glu Leu Lys Glu Tyr Ala Leu Glu Val Asp Met
            355                 360                 365

Asp Phe Val Arg Arg Ala Ile Lys Ala Ile Gly Gln Val Ala Ile Lys
370                 375                 380

Ile Glu Asp Ala Ser Ala Lys Cys Val Gln Ala Leu Glu Asp Leu Leu
385                 390                 395                 400

Ala Thr Lys Val Asn Tyr Val Val Gln Glu Val Val Val Ile Lys
                    405                 410                 415

Asp Ile Leu Arg Lys Tyr Pro Gly Tyr Glu Gly Val Ile Pro Ser Leu
                420                 425                 430

Cys Asn Tyr Ile Asp Glu Leu Asp Glu Ala Asn Ala Arg Gly Ser Leu
            435                 440                 445

Ile Trp Ile Val Gly Glu Tyr Ala Glu Lys Ile Ser Asn Ala Glu Glu
        450                 455                 460

Ile Leu Asp Gly Phe Val Asp Thr Phe Ser Glu Phe Thr Gln Thr
465                 470                 475                 480

Gln Leu Gln Ile Leu Thr Ala Val Val Lys Leu Phe Leu Lys Lys Pro
                485                 490                 495

Ser Gly Ala Gln Ser Leu Val Gln Lys Val Leu Gln Glu Ala Thr Thr
            500                 505                 510

Asn Asn Asp Asn Pro Asp Ile Arg Asp Arg Ala Tyr Val Tyr Trp Arg
            515                 520                 525

Leu Leu Ser Gly Asp Leu Glu Val Ala Lys Asn Ile Val Leu Ser Thr
            530                 535                 540

Lys Pro Thr Ile Ser Thr Thr Met Thr Ser Leu Pro Ala Thr Leu Leu
545                 550                 555                 560

Glu Gln Leu Leu Ser Glu Leu Ser Thr Leu Ala Ser Val Tyr His Lys
                565                 570                 575

Pro Pro Glu Ala Phe Val Gly Lys Gly Arg Phe Gly Ala Asp Glu Ile
            580                 585                 590

Gln Arg Ala Ala Ile Gln Glu Gln Arg Gln Asn Ala Ala Glu Asn Pro
            595                 600                 605

Ile Ala Val Ser Val Ala Asn Gly Ser Gly Ser Val Ser Gln Asn
610                 615                 620

Asn Ile Glu Asn Leu Leu Asp Ile Asp Phe Asp Gly Ala Ala Pro Ala
625                 630                 635                 640

Ser His Glu Gln Asn Ser Ala Thr Gly Thr Pro Asp Arg Met Gln Ser
                645                 650                 655

Pro Ala Thr Gly Gly Met Ala Asp Met Met Ser Met Phe Asp Ala Pro
                660                 665                 670

Pro Ala Gly Gly Ser Ala Ala Pro Ala Ala Pro Ala Gly Gly Met
            675                 680                 685

Asn Asp Leu Met Asn Gly Phe Glu Gly Leu Asn Phe Gly Gly Ala Thr
690                 695                 700

Thr Ser Glu Pro Leu Pro Ala Ala Met Gln Leu His Asn Ala Gln Ser
```

```
                    705                 710                 715                 720
Val Ser Gln Pro Lys Lys Asp Ser Asp Asp Leu Leu Gly Leu Leu
                    725                 730                 735

<210> SEQ ID NO 9
<211> LENGTH: 734
<212> TYPE: PRT
<213> ORGANISM: Trichoderma harzianum

<400> SEQUENCE: 9

Met Ala Val Asn Arg Ile Arg Gly Ala Phe Ala Ala Pro Arg Lys Gly
1               5                   10                  15

Glu Thr Phe Glu Leu Arg Ala Gly Leu Val Ser Gln Tyr Ala Tyr Glu
                20                  25                  30

Arg Lys Glu Ser Ile Gln Lys Thr Ile Met Ala Met Thr Leu Gly Lys
            35                  40                  45

Asp Val Ser Ala Leu Phe Pro Asp Val Leu Lys Asn Ile Ala Thr Ser
        50                  55                  60

Asp Leu Asp Gln Lys Lys Leu Val Tyr Leu Tyr Leu Met Asn Tyr Ala
65                  70                  75                  80

Lys Thr His Pro Asp Leu Cys Ile Leu Ala Val Asn Thr Phe Val Gln
                85                  90                  95

Asp Ser Glu Asp Pro Asn Pro Leu Val Arg Ala Leu Ala Ile Arg Thr
                100                 105                 110

Met Gly Cys Ile Arg Val Asp Lys Met Val Asp Tyr Met Glu Glu Pro
            115                 120                 125

Leu Arg Lys Thr Leu Arg Asp Glu Ser Pro Tyr Val Arg Lys Thr Ala
        130                 135                 140

Ala Ile Cys Val Ala Lys Leu Phe Asp Leu Asn Pro Ala Met Cys Ile
145                 150                 155                 160

Glu Asn Gly Phe Ile Glu Thr Leu Gln Glu Met Ile Gly Asp Pro Asn
                165                 170                 175

Pro Met Val Val Ala Asn Ser Val Gln Ala Leu Ala Glu Ile Ser Glu
                180                 185                 190

Thr Ala Pro Glu Thr Arg Ala Leu Leu Val Thr Pro Ala Val Leu Lys
            195                 200                 205

Lys Leu Leu Met Ala Met Asn Glu Cys Thr Glu Trp Gly Arg Ile Thr
        210                 215                 220

Ile Leu Thr Val Leu Ala Asp Tyr Val Ala Leu Asp Val Lys Glu Ser
225                 230                 235                 240

Glu His Ile Cys Glu Arg Val Ile Pro Gln Phe Gln His Val Asn Pro
                245                 250                 255

Ser Val Val Leu Ala Ala Val Lys Val Val Phe Ile His Met Lys Ser
                260                 265                 270

Ile Asn Pro Glu Leu Val Arg Ser Tyr Leu Lys Lys Met Ala Pro Pro
            275                 280                 285

Leu Val Thr Leu Val Ala Ser Ala Pro Glu Val Gln Tyr Val Ala Leu
        290                 295                 300

Arg Asn Ile Asp Leu Leu Leu Gln Ala Lys Pro Asp Ile Leu Ser Lys
305                 310                 315                 320

Glu Leu Arg Val Phe Phe Cys Lys Tyr Asn Asp Pro Tyr Val Lys
                325                 330                 335

Met Gln Lys Leu Glu Ile Met Val Arg Ile Ala Asn Glu Lys Asn Tyr
            340                 345                 350
```

```
Glu Gln Leu Leu Ser Glu Leu Lys Glu Tyr Ala Leu Glu Val Asp Met
            355                 360                 365

Asp Phe Val Arg Arg Ala Ile Lys Ala Ile Gly Gln Val Ala Ile Lys
    370                 375                 380

Ile Glu Asp Ala Ser Ala Lys Cys Val Gln Ala Leu Glu Asp Leu Leu
385                 390                 395                 400

Ala Thr Lys Val Asn Tyr Val Val Gln Glu Val Val Val Ile Lys
                405                 410                 415

Asp Ile Leu Arg Lys Tyr Pro Gly Tyr Glu Gly Val Ile Pro Ser Leu
            420                 425                 430

Cys Asn Tyr Ile Asp Glu Leu Asp Glu Ala Asn Ala Arg Gly Ser Leu
        435                 440                 445

Ile Trp Ile Val Gly Glu Tyr Ala Glu Lys Ile Ser Asn Ala Glu Glu
    450                 455                 460

Ile Leu Glu Gly Phe Val Asp Thr Phe Ser Glu Glu Phe Thr Gln Thr
465                 470                 475                 480

Gln Leu Gln Ile Leu Thr Ala Val Val Lys Leu Phe Leu Lys Lys Pro
                485                 490                 495

Ser Gly Ala Gln Ser Leu Val Gln Lys Val Leu Gln Glu Ala Thr Thr
            500                 505                 510

Asn Asn Asp Asn Pro Asp Ile Arg Asp Arg Ala Tyr Val Tyr Trp Arg
        515                 520                 525

Leu Leu Ser Gly Asp Leu Glu Val Ala Lys Ser Ile Val Leu Ser His
    530                 535                 540

Lys Pro Thr Ile Ser Thr Thr Met Thr Ser Leu Pro Ala Thr Leu Leu
545                 550                 555                 560

Glu Gln Leu Leu Ser Glu Leu Ser Thr Leu Ala Ser Val Tyr His Lys
                565                 570                 575

Pro Pro Glu Ala Phe Val Gly Lys Gly Arg Phe Gly Ala Asp Glu Ile
            580                 585                 590

Gln Arg Ala Ala Ile Gln Glu Gln Arg Gln Asn Ala Ala Glu Asn Pro
        595                 600                 605

Ile Ala Ala Ser Val Ala Ala Ala Ala Asn Gly Ser Ser Ser Val
    610                 615                 620

Ser Gln Ser Asn Ile Glu Asn Leu Leu Asp Ile Asp Phe Asp Gly Ala
625                 630                 635                 640

Ala Pro Ala Ser Gln Glu Gln Thr Ser Ala Thr Gly Thr Pro Asp Arg
                645                 650                 655

Met Ala Ser Pro Ala Thr Gly Gly Met Ala Asp Met Met Ser Met Phe
            660                 665                 670

Asp Ala Pro Ser Ala Ser Gly Ala Pro Ala Ala Pro Ala Gly Gly
        675                 680                 685

Met Asn Asp Leu Met Asn Gly Phe Glu Gly Leu Asn Phe Gly Ala Ala
    690                 695                 700

Asn Ala Ser Gln Pro Leu Pro Ala Ala Met Gln Leu His Gly Gly Gly
705                 710                 715                 720

Ser Glu Pro Lys Lys Asp Ser Asp Asp Leu Leu Gly Leu Leu
                725                 730

<210> SEQ ID NO 10
<211> LENGTH: 734
<212> TYPE: PRT
<213> ORGANISM: Trichoderma guizhouense

<400> SEQUENCE: 10
```

```
Met Ala Val Asn Arg Ile Arg Gly Ala Phe Ala Ala Pro Arg Lys Gly
1               5                   10                  15

Glu Thr Phe Glu Leu Arg Ala Gly Leu Val Ser Gln Tyr Ala Tyr Glu
            20                  25                  30

Arg Lys Glu Ser Ile Gln Lys Thr Ile Met Ala Met Thr Leu Gly Lys
                35                  40                  45

Asp Val Ser Ala Leu Phe Pro Asp Val Leu Lys Asn Ile Ala Thr Ala
        50                  55                  60

Asp Leu Asp Gln Lys Lys Leu Val Tyr Leu Tyr Leu Met Asn Tyr Ala
65                  70                  75                  80

Lys Thr His Pro Asp Leu Cys Ile Leu Ala Val Asn Thr Phe Val Gln
                85                  90                  95

Asp Ser Glu Asp Pro Asn Pro Leu Val Arg Ala Leu Ala Ile Arg Thr
                100                 105                 110

Met Gly Cys Ile Arg Val Asp Lys Met Val Asp Tyr Met Glu Glu Pro
            115                 120                 125

Leu Arg Lys Thr Leu Arg Asp Glu Ser Pro Tyr Val Arg Lys Thr Ala
130                 135                 140

Ala Ile Cys Val Ala Lys Leu Phe Asp Leu Asn Pro Ala Met Cys Ile
145                 150                 155                 160

Glu Asn Gly Phe Ile Glu Thr Leu Gln Glu Met Ile Gly Asp Pro Asn
                165                 170                 175

Pro Met Val Val Ala Asn Ser Val Gln Ala Leu Ala Glu Ile Ser Glu
            180                 185                 190

Thr Ala Pro Glu Thr Arg Ala Leu Val Thr Pro Ala Val Leu Lys
                195                 200                 205

Lys Leu Leu Met Ala Met Asn Glu Cys Thr Glu Trp Gly Arg Ile Thr
210                 215                 220

Ile Leu Thr Val Leu Ala Asp Tyr Val Ala Leu Asp Val Lys Glu Ser
225                 230                 235                 240

Glu His Ile Cys Glu Arg Val Ile Pro Gln Phe Gln His Val Asn Pro
                245                 250                 255

Ser Val Val Leu Ala Ala Val Lys Val Phe Ile His Met Lys Ser
            260                 265                 270

Ile Asn Pro Glu Leu Val Arg Ser Tyr Leu Lys Lys Met Ala Pro Pro
                275                 280                 285

Leu Val Thr Leu Val Ala Ser Gln Pro Glu Val Gln Tyr Val Ala Leu
            290                 295                 300

Arg Asn Ile Asp Leu Leu Leu Gln Ala Lys Pro Asp Ile Leu Ser Lys
305                 310                 315                 320

Glu Leu Arg Val Phe Phe Cys Lys Tyr Asn Asp Pro Pro Tyr Val Lys
                325                 330                 335

Met Gln Lys Leu Glu Ile Met Val Arg Ile Ala Asn Glu Lys Asn Tyr
            340                 345                 350

Glu Gln Leu Leu Ser Glu Leu Lys Glu Tyr Ala Leu Glu Val Asp Met
                355                 360                 365

Asp Phe Val Arg Arg Ala Ile Lys Ala Ile Gly Gln Val Ala Ile Lys
        370                 375                 380

Ile Glu Asp Ala Ser Ala Lys Cys Val Gln Ala Leu Glu Asp Leu Leu
385                 390                 395                 400

Ala Thr Lys Val Asn Tyr Val Val Gln Glu Val Val Val Ile Lys
                405                 410                 415
```

Asp Ile Leu Arg Lys Tyr Pro Gly Tyr Gly Val Ile Pro Ser Leu
                420                 425                 430

Cys Asn Tyr Ile Asp Glu Leu Asp Glu Ala Asn Ala Arg Gly Ser Leu
            435                 440                 445

Ile Trp Ile Val Gly Glu Tyr Ala Glu Lys Ile Ser Asn Ala Glu Glu
        450                 455                 460

Ile Leu Glu Gly Phe Val Asp Thr Phe Ser Glu Glu Phe Thr Gln Thr
465                 470                 475                 480

Gln Leu Gln Ile Leu Thr Ala Val Val Lys Leu Phe Leu Lys Lys Pro
                485                 490                 495

Ser Gly Ala Gln Ser Leu Val Gln Lys Val Leu Gln Glu Ala Thr Thr
            500                 505                 510

Asn Ser Asp Asn Pro Asp Ile Arg Asp Arg Ala Tyr Val Tyr Trp Arg
        515                 520                 525

Leu Leu Ser Gly Asp Leu Glu Val Ala Lys Asn Ile Val Leu Ser His
530                 535                 540

Lys Pro Thr Ile Ser Thr Thr Met Thr Ser Leu Pro Ala Thr Leu Leu
545                 550                 555                 560

Glu Gln Leu Leu Ser Glu Leu Ser Thr Leu Ala Ser Val Tyr His Lys
                565                 570                 575

Pro Pro Glu Ala Phe Val Gly Lys Gly Arg Phe Gly Ala Asp Glu Ile
            580                 585                 590

Gln Arg Ala Ala Ile Gln Glu Gln Arg Gln Asn Ala Ala Glu Asn Pro
        595                 600                 605

Ile Ala Ala Ser Val Ala Ala Ala Ala Asn Gly Ser Ser Ser Val
610                 615                 620

Ser Gln Ser Asn Ile Glu Asn Leu Leu Asp Ile Asp Phe Asp Gly Ala
625                 630                 635                 640

Ala Pro Ala Ser Gln Glu Gln Ser Ser Ala Ala Gly Thr Pro Asp Arg
                645                 650                 655

Met Ala Ser Pro Ala Thr Gly Gly Met Ala Asp Met Met Ser Met Phe
            660                 665                 670

Asp Ala Pro Ser Ala Ser Gly Ala Pro Ala Ala Ala Pro Ala Gly Gly
        675                 680                 685

Met Asn Asp Leu Met Asn Gly Phe Glu Gly Leu Asn Phe Gly Ala Ala
690                 695                 700

Asn Gly Ser Gln Pro Leu Pro Ala Gly Met Gln Leu His Gly Gly Gly
705                 710                 715                 720

Ser Glu Pro Lys Lys Asp Ser Asp Asp Leu Leu Gly Leu Leu
                725                 730

<210> SEQ ID NO 11
<211> LENGTH: 859
<212> TYPE: PRT
<213> ORGANISM: Trichoderma reesei

<400> SEQUENCE: 11

Met Pro His Arg Glu Arg Gly Lys Gln Arg Glu Gly Gly Asp Ser Tyr
1               5                   10                  15

Arg Pro Ser Arg Pro Ala Arg Ser Arg Ser Arg Ser Pro Pro
                20                  25                  30

Arg Ala Pro Val Pro Val Arg Thr Glu Glu Lys Gln Ala Ala Ala
            35                  40                  45

Lys Ala Glu Tyr Glu Lys Leu Leu Asn Met Arg Ser Gly Gly Thr Tyr
        50                  55                  60

-continued

```
Ile Pro Pro Ala Arg Leu Arg Ala Leu Gln Ala Gln Ile Thr Asp Lys
 65                  70                  75                  80

Ser Ser Lys Glu Tyr Gln Arg Met Ala Trp Glu Ala Leu Lys Lys Ser
                 85                  90                  95

Ile Asn Gly Leu Ile Asn Lys Val Asn Thr Ala Asn Ile Lys His Ile
            100                 105                 110

Val Pro Glu Leu Phe Gly Glu Asn Leu Val Arg Gly Arg Gly Leu Phe
            115                 120                 125

Cys Arg Ser Ile Met Lys Ala Gln Ala Ala Ser Leu Pro Phe Thr Pro
130                 135                 140

Ile Tyr Ala Ala Met Ala Ala Ile Val Asn Thr Lys Leu Pro Gln Val
145                 150                 155                 160

Gly Glu Leu Leu Val Lys Arg Leu Ile Met Gln Phe Arg Lys Gly Phe
                165                 170                 175

Lys Arg Asn Asp Lys Ala Val Cys Leu Ser Ser Thr Thr Phe Leu Ala
            180                 185                 190

His Leu Ile Asn Gln Gln Val Gln His Glu Met Leu Ala Gly Gln Ile
            195                 200                 205

Leu Leu Leu Leu Leu His Lys Pro Thr Asp Asp Ser Val Glu Ile Ala
210                 215                 220

Val Gly Phe Cys Lys Glu Val Gly Gln Tyr Leu Glu Glu Met Gln Pro
225                 230                 235                 240

Ala Ile Ser Met Ala Val Phe Asp Gln Phe Arg Asn Ile Leu His Glu
                245                 250                 255

Ser Asp Ile Asp Lys Arg Thr Gln Tyr Met Ile Glu Val Leu Phe Gln
            260                 265                 270

Ile Arg Lys Asp Lys Phe Lys Asp His Pro Ala Ile Lys Glu Glu Leu
            275                 280                 285

Asp Leu Val Glu Glu Asp Gln Ile Thr His Lys Val Glu Leu Asp
290                 295                 300

Gly Glu Ile Asp Val Gln Asp Gly Leu Asn Ile Phe Lys Tyr Asp Pro
305                 310                 315                 320

Glu Trp Glu Glu His Glu Glu Ala Tyr Lys Arg Leu Lys Ala Glu Ile
                325                 330                 335

Leu Gly Glu Ala Ser Asp Asp Glu Glu Gly Asp Glu Asp Glu Asp Glu
            340                 345                 350

Asp Glu Ser Ser Glu Asp Glu Glu Asn Glu Glu Thr Lys Ala Met Glu
            355                 360                 365

Ile Lys Asp Gln Ser Asn Ala Asp Leu Val Asn Leu Arg Arg Thr Ile
            370                 375                 380

Tyr Leu Thr Ile Met Ser Ser Ala Asp Pro Glu Glu Ala Val His Lys
385                 390                 395                 400

Leu Met Lys Ile Asn Leu Pro Val Gly Gln Glu Pro Glu Leu Pro Ser
                405                 410                 415

Met Ile Val Glu Cys Cys Ser Gln Glu Lys Thr Tyr Thr Lys Phe Phe
            420                 425                 430

Gly Leu Ile Gly Glu Arg Phe Ala Lys Ile Asn Arg Leu Trp Cys Asp
            435                 440                 445

Leu Phe Glu Gln Ala Phe Val Lys Tyr Tyr Glu Thr Ile His Arg Tyr
450                 455                 460

Glu Asn Asn Lys Leu Arg Asn Ile Ala Met Leu Phe Gly His Met Phe
465                 470                 475                 480
```

```
Ala Ser Asp Ala Leu Gly Trp His Cys Leu Ser Val Ile His Leu Asn
                485                 490                 495

Glu Glu Glu Thr Thr Ser Ser Arg Ile Phe Ile Lys Ile Leu Phe
            500                 505                 510

Gln His Ile Ser Glu Glu Ile Gly Leu Ala Lys Leu Arg Ala Arg Met
            515                 520                 525

Thr Asp Glu Thr Leu Arg Pro Ser Leu Glu Gly Leu Phe Pro Arg Glu
530                 535                 540

Asn Pro Arg Asn Ile Arg Phe Ser Ile Asn Tyr Phe Thr Ser Ile Gly
545                 550                 555                 560

Met Gly Val Leu Thr Glu Glu Met Arg Glu His Leu Met Asn Met Pro
                565                 570                 575

Lys Pro Ala Leu Pro Ala Pro Ala Ala Gln Asp Arg Ser Asp Thr Asp
                580                 585                 590

Ser Val Ser Ser Tyr Ser Ser Tyr Thr His Ser Ser Tyr Ser Ser Arg
            595                 600                 605

Ser Arg Ser Arg Ser Arg Ser Val Gly Arg Arg Ser Gly Gly Arg Gly
    610                 615                 620

Arg Ser Leu Ser Arg Thr Pro Pro Arg Gly Ala Arg Ser Arg Ser
625                 630                 635                 640

Tyr Ser Asp Asp Ser Arg Ser Pro Ser Arg Ser Arg Ser Arg Ser Arg
                645                 650                 655

Ser Asp Ser Val Ser Thr Arg Gly Arg Arg Ala Ser Ser Tyr Ser Ala
                660                 665                 670

Ser Pro Pro Arg Arg Gly Gly Arg Arg Val Ala Ser Arg Ser Arg Ser
                675                 680                 685

Tyr Ser Ser Gly Ser Ser Arg Ser Pro Pro Arg Asn Arg Gly Arg
690                 695                 700

Ala Arg Ser Asn Ser Tyr Ser Ser Tyr Ser Arg Ser Pro Ser Ser Ser
705                 710                 715                 720

Pro Arg Arg Gly Arg Asp Ala Asp Ser Ala Ser Pro Pro Arg Arg
                725                 730                 735

Gly Arg Pro Arg Gln Ser Pro Pro Gly Gly Pro Ala Gly Arg Arg Asn
                740                 745                 750

Ser Ser Ser Val Gly Ser Gly Gly Pro Arg Lys Lys Pro Arg Arg Asp
            755                 760                 765

Ser Arg Ser Pro Ser Arg Asp Tyr Ser Ser Arg Ser Pro Ser Arg Ser
    770                 775                 780

Pro Ser Arg Ser Arg Ser Pro Pro Ala Ala Arg Gly Arg Arg Gly
785                 790                 795                 800

Ser Tyr Thr Pro Ser Arg Ser Arg Ser Pro Pro Arg Arg Val Arg
                805                 810                 815

Asp Gly Ser Pro Gly Arg Leu Arg Gly Gly Arg Ser Pro Ser Pro Pro
                820                 825                 830

Leu Pro Val Lys Arg Arg Tyr Asp Ser Glu Ser Val Ser Arg Ser
                835                 840                 845

Pro Pro Pro Leu Lys Arg Gly Arg Arg Asp Asn
    850                 855

<210> SEQ ID NO 12
<211> LENGTH: 2580
<212> TYPE: DNA
<213> ORGANISM: Trichoderma reesei

<400> SEQUENCE: 12
```

-continued

```
atgccgcacc gcgagcgcgg caagcagcga gaaggcggcg actcgtaccg cccctcgagg      60
ccagcgcgtt cacgctcgcg ctcgcgatcg ccgcctcgcg cgccggtgcc cgtgcggacg     120
gaggaggaga agcaggcggc ggcaaaggcc gagtacgaga agctgctcaa catgcggtcg     180
ggcggcacgt acatcccgcc ggcgaggctg agggcgctgc aggcgcagat cacggacaag     240
agcagcaagg agtaccagcg gatggcgtgg gaggcgctca agaagagcat caacggcctg     300
atcaacaagg tcaacacggc caacatcaag cacattgtgc ccgagctgtt tggcgagaac     360
ctggtgcgcg ccgcggcct cttctgccgc tccatcatga aggcccaggc cgccagtttg      420
cccttcacgc ccatctacgc cgccatggcc gccattgtca acaccaagct gccgcaggtc     480
ggcgagctgc tggtcaagcg cctcatcatg cagttccgca agggcttcaa gcgcaacgac     540
aaggccgtct gtctgtcgtc gaccaccttc ctcgcccacc tcatcaacca gcaggtgcag     600
cacgagatgc tggccggcca gatcctgctg ctgctgctgc acaagccgac cgacgacagc     660
gtcgagattg ccgtgggctt ctgcaaggag gttggccagt acctcgagga gatgcagcct     720
gccatttcca tggccgtctt cgaccagttc cgcaacatcc tccacgagtc cgacattgac     780
aagcgaacgc agtacatgat tgaggtgctc ttccagatca ggaaggacaa gttcaaggat     840
cacccggcca tcaaggagga gctggacttg gtggaggagg aggaccagat cacgcacaag     900
gtggagcttg atggcgagat tgatgtgcag gacggactca acatcttcaa gtacgacccg     960
gagtgggagg agcatgagga ggcatacaag aggctcaagg cggagattct gggcgaagcc    1020
agcgatgacg aggagggcga cgaggacgag gacgaggacg agagctccga agatgaagaa    1080
aacgaagaga caaaggccat ggagatcaag gaccagtcta acgccgactt ggtcaaccta    1140
cggaggacca tctacctcac catcatgtcg agcgccgacc cagaggaagc agttcacaag    1200
ctgatgaaga tcaacctgcc cgtcggccag gaacccgagc tgccctcgat gattgtcgag    1260
tgttgctcgc aggagaagac gtacaccaag ttctttggct tgatcggcga gcgtttcgcc    1320
aagatcaatc ggctgtggtg cgacctcttt gagcaggcct ttgtcaagta ctacgagacg    1380
atccaccgat acgaaaacaa caagctgcgc aacattgcca tgctgtttgg ccacatgttt    1440
gcttccgacg ctctgggctg gcactgcctt tccgtcattc acctcaacga ggaggagacc    1500
acgtcgagca gccgcatctt catcaagatt ctgttccagc acatttccga ggaaatcggc    1560
ctggctaagc tccgggcacg catgactgac gagacgctgc ggcccagcct cgaaggcctc    1620
ttccccagag agaaccctcg caacatccga ttctccatca actacttcac cagcatcggc    1680
atgggtgtac tgaccgagga gatgcgagag cacctcatga acatgccaa gcctgcgctg     1740
cccgcccctg ctgctcagga ccgctcggat acggactccg tctcgagcta ttcgtcttac    1800
actcactcat catactcttc ccgctcgcgc tcacggtccc gatctgtggg tcgtcggagc    1860
ggcggtcgag gccgatcgct ttcccgaact ccgcctcgac gtggcgcaag gagccgatcc    1920
tactctgacg actcacggtc accgtcgcgg tcaagatcac gatcccgctc cgattccgtc    1980
tctactcgtg ggcgaaggcg agcgtcgtac tcggccagtc ctccccggcg tggtggccgt    2040
cgggttgcca gcagaagccg aagctactcg tcgggctcct cacggtctcc gccaccacgg    2100
aaccgcggtc gcgcacgaag caactcgtat agttcctaca gccgctctcc atcttcttca    2160
ccacgacgcg gcagagacgc agactcggcc agcccgcctc cgcgaagggg tcgaccgcgc    2220
cagagcccac caggcggtcc cgcaggtcga aggaacagcc cgtctgtcgg cagcggaggg    2280
ccccgcaaga agccccgacg ggacagccga tcgccgtctc gcgactattc gtcccggtcc    2340
```

```
ccgtctcggt cgccgtcgag atctcgatcg cctccgccgg ctgcgcgtgg ccgaaggggc    2400
tcttatacgc cgtcacgcag ccgcagcccg cctccgcgca gggtgaggga tggctcgccg    2460
ggtcgtctga ggggtgggag gtcgcctagt cctcctttgc cggtgaagag gaggcggtat    2520
gatagcgaga gtgtttctcg gtcgccgcct cctttgaagc gcgggagaag ggataactaa    2580
```

<210> SEQ ID NO 13
<211> LENGTH: 543
<212> TYPE: PRT
<213> ORGANISM: Trichoderma reesei

<400> SEQUENCE: 13

```
Met Thr Val Leu Thr Ser Pro Leu Ala Ser Tyr Asn Val Ala Asn Lys
1               5                   10                  15

Leu Tyr Lys Thr Thr Leu Leu Asn Thr Val Cys Leu Val Ala Gly Leu
            20                  25                  30

Ser Ile Phe Phe Phe Gly Tyr Asp Gln Gly Leu Met Gly Gly Val Asn
        35                  40                  45

Thr Thr Arg Asp Tyr Ala Glu Arg Met Gly Phe Gly His Trp Asp Glu
    50                  55                  60

Asp Gln Asn Ile Val Val Val Asp Lys Pro Leu Leu Gln Gly Gly Ile
65                  70                  75                  80

Val Ala Val Tyr Tyr Leu Pro Gly Thr Leu Cys Gly Cys Leu Leu Gly
                85                  90                  95

Gly Trp Leu Gly Asp Arg Tyr Gly Arg Ile Lys Thr Ile Ala Ile Ala
            100                 105                 110

Cys Ala Trp Ser Val Cys Ala Ala Leu Gln Ala Ser Ala Met Asn
            115                 120                 125

Ala Asn Trp Met Phe Cys Ala Arg Val Leu Asn Gly Val Gly Thr Gly
        130                 135                 140

Ile Leu Asn Ala Ile Thr Pro Val Trp Ala Thr Glu Thr Ala Ala His
145                 150                 155                 160

Thr Ser Arg Gly Gln Phe Val Ser Ile Glu Phe Thr Leu Asn Ile Leu
                165                 170                 175

Gly Val Val Val Ala Tyr Trp Leu Glu Phe Gly Thr Ser Lys Tyr His
            180                 185                 190

Asp Asn Thr Ser Ser Phe Ile Trp Arg Phe Pro Val Ala Phe Gln Ile
        195                 200                 205

Leu Pro Leu Ile Leu Leu Phe Leu Ile Ile Trp Ile Met Pro Glu Ser
    210                 215                 220

Pro Arg Trp Leu Val Lys Val Gly Arg Glu Glu Ala Arg Phe Ile
225                 230                 235                 240

Leu Gly Arg Leu Arg Gly Asn Glu Gly Glu Asp Gly Leu Lys Ala Glu
                245                 250                 255

Ala Glu Tyr Asn Asp Ile Val Asn Ile His Lys Leu Glu Val Asp Thr
            260                 265                 270

Ala Lys Gln Gln Ser Tyr Phe Ser Met Phe Phe Gly Ile Gly Ser Gly
        275                 280                 285

Lys Leu His Thr Gly Arg Arg Val Gln Leu Val Ile Trp Leu Gln Ile
    290                 295                 300

Leu Gln Glu Trp Ile Gly Ile Ala Gly Ile Thr Ile Tyr Gly Pro Glu
305                 310                 315                 320

Ile Phe Thr Ile Ala Gly Ile Ser Ala Lys Asp Arg Leu Trp Val Ser
                325                 330                 335
```

```
Gly Ile Asn Asn Ile Thr Tyr Met Phe Ala Thr Leu Ile Cys Val Phe
                340                 345                 350

Thr Ile Asp Arg Ile Gly Arg Arg Trp Thr Leu Tyr Trp Gly Ala Val
            355                 360                 365

Gly Gln Gly Ile Cys Met Phe Val Ala Gly Gly Leu Ala Arg Ala Thr
        370                 375                 380

Ile Asn Ala Ser Gly Lys Ala Ser Gln Ser His Ile Gly Gly Ala Ala
385                 390                 395                 400

Thr Phe Phe Val Phe Leu Tyr Thr Ala Ile Phe Gly Ala Thr Trp Leu
                405                 410                 415

Thr Val Pro Trp Leu Tyr Pro Ala Glu Ile Phe Pro Leu Gln Val Arg
            420                 425                 430

Ala Lys Gly Asn Ala Trp Gly Val Val Gly Trp Ser Ile Gly Asn Gly
        435                 440                 445

Trp Cys Val Leu Leu Pro Thr Ile Phe Lys Ala Leu Asn Glu Lys
    450                 455                 460

Thr Leu Tyr Ile Phe Gly Ala Val Asn Ala Leu Ser Ile Leu Val Val
465                 470                 475                 480

Trp Ala Leu Tyr Pro Glu Ser Asn Gln Arg Thr Leu Glu Glu Met Asp
                485                 490                 495

Leu Val Phe Ala Ser Asp Ser Ile Trp Ala Trp Glu Ala Glu Arg Asn
            500                 505                 510

Phe Ala Lys Leu Lys Ala Glu Asn Pro Asp Leu Val Gln Gly Ser Thr
        515                 520                 525

Asn His Gly Val Val Asp Ile Glu Gln Val Ala Glu Pro Lys Glu
    530                 535                 540

<210> SEQ ID NO 14
<211> LENGTH: 1870
<212> TYPE: DNA
<213> ORGANISM: Trichoderma reesei

<400> SEQUENCE: 14
atgaccgtcc tcacctcacc tctggccagc tataatgtgg ccaacaagct gtacaaaacc      60
actctgctca acaccgtctg cctcgtggcc ggactgtcga tcttcttctt cggctatgat     120
cagggattga tgggcggtgt taacacgacg cgcgactatg ccgagcgcat gggctttggc     180
cactgggacg aagaccagaa cattgtcgtc gtcgataagc cgctgctgca gggcggtatc     240
gtagctgtct actatctccc cggaacgctg tgcggttgtc tgcttggcgg ttggcttggt     300
gatcgctatg ccgtatcaa acaattgcc attgcctgtg cgtggagtgt ctgcgcagcc       360
gccctgcagg cctcagctat gaatgcgaac tggatgtttt gcggtatgtc gatgattctt     420
ggacaatcac aaccgaacta ttactgatga tgagatgaaa cagcccgcgt ctgaacggc      480 gtcggcactg gaatcttgaa cgcaatcacg cctgtgtggg caaccgagac tgctgctcac     540
acttctcgag gccagttcgt ttccattgag ttcaccctca acattcttgg tgttgttgta    600
gcctactggc tggaattgta cgtgcctcct cactcaggat ccccagtctt gtggaaagtc     660
tccctaatgc ggtggcagtg gtacttctaa atatcacgac aacacatcct ccttcatctg     720
gagattcccg gtcgccttcc agatcctccc cctaatcctt ctgttcctca tcatctggat     780
catgcctgaa tcccccgct ggctcgtcaa agtgggtcgt gaagaagagg ctcgcttcat      840
ccttggtcgt ctccgtggca atgagggcga ggacggcctc aaggcggaag cagagtacaa     900
tgatattgtc aacatccaca agcttgaagt agacaccgcc aagcagcaga gctacttctc     960
```

| | |
|---|---|
| catgttctttt ggcattgggt ctggaaagct acacactggc cggcgcgtgc agctggtcat | 1020 |
| ctggctccag atattgcaag agtggatcgg tattgcggga atcaccattt acggccctga | 1080 |
| gatctttacg attgctggca tcagcgcaaa ggacagactc tgggttagcg ggatcaacaa | 1140 |
| tatcacatac atggtacgtt tagccaacac ctcctcacct caaagattcc atcacactaa | 1200 |
| cacgggagca gttcgccaca ctgatctgcg tcttcaccat cgatcgcata ggtcgccgtt | 1260 |
| ggactctgta ctggggagct gtcggccagg gcatttgcat gttcgtcgcc ggtgcctcg | 1320 |
| ctcgcgcaac catcaatgcc tcaggcaaag caagccagag ccacatcggc ggcgctgcaa | 1380 |
| cattctttgt gttcctctac actgccattt tcggcgctac ctggctgacg gttccttggt | 1440 |
| tgtatccggc cgagatttttc cctctgcagg ttagagccaa gggaaatgcc tggggtgtcg | 1500 |
| ttggctggtc cattggcaac ggctggtgtg taagtgcact tttcattctc ctctcccgtc | 1560 |
| tgggctcttc tggtctaatc ttctctaggt gctcctgctt cctacgatct tcaaggcgct | 1620 |
| caacgaaaag acactctaca tttttggcgc cgtcaacgcc ctgtccatcc tcgtcgtgtg | 1680 |
| ggctctgtac cccgaatcga atcaacgaac tctagaggag atggacctcg tctttgctag | 1740 |
| cgacagcatc tgggcctggg aggctgagcg taattttgcc aagctcaagg ctgaaaaccc | 1800 |
| ggatcttgtt cagggctcaa caaaccacgg agttgtagat attgagcaag ttgccgagcc | 1860 |
| aaaggagtag | 1870 |

<210> SEQ ID NO 15
<211> LENGTH: 7802
<212> TYPE: DNA
<213> ORGANISM: Artificial Sequence
<220> FEATURE:
<223> OTHER INFORMATION: DNA fragment for transformation

<400> SEQUENCE: 15

| | |
|---|---|
| ggtaccctga gagaacaggc agcatcttgc gagttctatg aggtgtctga taaaaaaaca | 60 |
| atacattact tatagacata ccactgccga caacttcatc tccatatcct ctgttccgtc | 120 |
| taactgattc gctcgctgtt ggatgatgac tcagcgtcgg ttggcctacg gtacatgtag | 180 |
| ggaggctgtc gagcaaccaa acccgcctgc taagctcatg cctggcctgt actgtatgaa | 240 |
| tccgcaacat aagctgcaac tcttcaaccc ctcgacagcc tgactcgcca ttccagaggc | 300 |
| cacgacacgc agccgttgct ggaggctctg ccgctagcga tttcctcgac agcctctgct | 360 |
| attccttctc ggctgtcctt ccaacaccgc tgttgtcgac tacactcgca gacgccttcg | 420 |
| aacacccgag acagcgtcac ccccagacac gggaccaaca ccttcgtgcc ctcctcctc | 480 |
| ctcctcctcc caccaactcc tcgacgatgg cggtgaatcg catccggggc gccttttgccg | 540 |
| cgcctcggaa gggagagaca ttcgagctgc gggccggcct ggtgtcgcag tatgcctacg | 600 |
| agcggaagga gtccatccag aagaccatca tggccatgac gctgggcaag gacgtgtccg | 660 |
| ccctgttccc agacgtcttg aagaacattg ccacgtccga cctggaccag aagaagctgg | 720 |
| tctacctcta cctcatgtat gtggctgcag acaatggccg accatgatca cacacacgga | 780 |
| gcgaaggacg agatactgcc tgacgtggcg atgcggtgct aacgtggagt gtgaccccag | 840 |
| gaactacgca aagacacacc cagacctctg cattctcgcc gtcaacacgt tcgtgcaaga | 900 |
| ctcggaagac ccgaacccgc tggtgcgagc gctggccatc cgcacaatgg gctgcatccg | 960 |
| ggtggacaag atggtcgact acatggagga gccgctgcgg aagacgctgc gggacgagtc | 1020 |
| gccgtacgtg cgcaagacgg ccgccatctg cgtggccaag ctgttcgacc tgaacccggc | 1080 |
| catgtgcatc gagaacggct tcatcgagac gctgcaggag atgattggcg acccgaaccc | 1140 |

```
catggtggtc gcaaactcgg tccaggcgct ggccgagatt agcgagacgg cgcccgagac    1200
gcgggcgctg ctggtgacgc ccccggtgct caagaagctg cttatggcca tgaacgaatg    1260
caccgaatgg ggtagaatca ccattctgac cgtgctggca gactacgctg ccaccgacgt    1320
caaggagtcg gagcacatct gcgagagggt cattccgcag ttccagcacg tcaaccctag    1380
cgtggtcctg gctgctgtca aggtggtctt tattcatatg aagtcgatta acccggagct    1440
cgtgcggtca tatcttaaga agatggcgcc tccactcggt gcgttccgat catgtccccg    1500
atttgacatc tgagaagaca tgacgtgact atgctaacac tgcagcttgt atacagtcac    1560
actggttgct tctgccccg aggtcaaata cgtcgctctc agaaacattg atctgctcct    1620
tcaagccaag cccgacatcc tgagcaaaga gttaagagtc ttcttttgca aatacaacga    1680
cccgccgtac gtcaagatgc aaaagctgga aatcatggtc aggatagcaa acgaaaagaa    1740
ctacgagcag ctcctgtctg agctcaagga atacgccctg gaagtggaca tggactttgt    1800
gcgccgagcc atcaaggcca tcggccaggt ggccatcaag attgaggagg ccagtggcaa    1860
gtgcgtgcag gcgctggaag atcttctcgc taccaaggtc aactacgtgg tgcaagaggt    1920
tgtcgtggtc atcaaagata tcctgcgaaa gtaccccggt tacgagggcg tgatcccctc    1980
gctctgcaac tacattgacg agctcgacga ggccaatgct cgtggatccc tcatctggat    2040
tgtgggagag tacgccgaga agattagcaa cgctgaggag attctggagg ttttgtaga    2100 cacctttttg gaggagttca ctcaggtatg tggagagctg tggaaaagtc ggggattttg    2160
gctaatcgaa ctgcagacac aactccagat ccttacagct gttgttaagc tgttttgaa    2220 gaagccgagt ggcgcgcagg gcctggttca gaaggtgctg caggaggcaa caaccaacaa    2280
cgacaacccc gatatccgcg acagagcata cgtctactgg cgattgttat cgggagattt    2340
ggaggtggcc aaggtaggag tcgttggcgt cctttgatga gagctgcgca tactgacgga    2400
tctcaagaac attgtcctgt cacagaagcc gaccatttca acaacaatga caagcctgcc    2460
gactgcgcta ctggagcagc tgctgtcgga gctgtcaact ctggcgtcgg tataccacaa    2520 gccccggaa gcctttgtcg gcaagggccg gttcggtgcc gacgagatcc agcgagccgc    2580
catccaggag cagcgccaga acgccgcgga aaacccatc gccgcatccg tggctgccgc    2640 cgccgcaat ggctcctcgt cggtctcgca aacaacatt gagaacctgc tggacattga    2700
ctttgacggc gcagcaccgg cctctcagga gcagaacagc gcggcgggaa cacctgaccg    2760
ggtgtcgagc ccggccacgg gtggcatggc cgacatgatg agcatgtttg atgcgcctcc    2820
ggctggcagc tctggaggtg ctccgtccgg cggcatgaac gacttgatga acggatttga    2880
ggggctcaac tttggggcca cgagtacaaa tcagccgttg ccggcggcga tgcagctgca    2940
caatgcgcaa ggcggctctc agccgaagaa ggatagcgat gatctttttgg gtttgttgta    3000 aatgttggag gagcgtatat gcatgcaagc agcaagccag aaggggagaa gaatcgacaa    3060
gagagactgg aggaggaggc aagggagggg ggggttctt ggaggctggg aaaatatagt    3120
taataagtga tgcataggta tttgatgtcc tgtgagatat atacatgtta tgaagatata    3180
atttgagttg tctataccct tttagacttt tttcgagttg atgccagcag catcggcttc    3240
ggctcgtaag cgtttccact cgtcgtatct cttttgttg atatccgtct tggcagcggc    3300
cgcctagtca tcattggata ggcagattac tcagcctgaa tgacatcaac atgttaccca    3360
tgatacaata ggtcacacaa acaagcgcta agatgcactt ggtatgacaa gcccagtagt    3420
ccgtttcaaa agacctagat gatgaactac aacatgaggt gttgcctcct gatccagtcc    3480
```

```
aactgcaaac gctgatgtat actcaatcaa gcctgatgta aatgctgcga ctcgattcgc    3540
tggatatgaa gatcaaagag agctctgatg ggtccaatat agccgggttt tgttaggaca    3600
gtccaccaca ccgatattag aattggtcaa gcaccttatc atttcataga gattgcggtt    3660
tctagatcta cgccaggacc gagcaagccc agatgagaac cgacgcagat ttccttggca    3720
cctgttgctt cagctgaatc ctggcaatac gagatacctg ctttgaatat tttgaatagc    3780
tcgcccgctg gagagcatcc tgaatgcaag taacaaccgt agaggctgac acggcaggtg    3840
ttgctaggga gcgtcgtgtt ctacaaggcc agacgtcttc gcggttgata tatatgtatg    3900
tttgactgca ggctgctcag cgacgacagt caagttcgcc ctcgctgctt gtgcaataat    3960
cgcagtgggg aagccacacc gtgactccca tctttcagta aagctctgtt ggtgtttatc    4020
agcaatacac gtaatttaaa ctcgttagca tggggctgat agcttaatta ccgtttacca    4080
gtgccgcggt tctgcagctt ccttggccc gtaaaattcg gcgaagccag ccaatcacca    4140
gctaggcacc agctaaaccc tataattagt ctcttatcaa caccatccgc tcccccggga    4200
tcaatgagga gaatgagggg gatgcggggc taaagaagcc tacataaccc tcatgccaac    4260
tcccagttta cactcgtcga gccaacatcc tgactataag ctaacacaga atgcctcaat    4320
cctgggaaga actggccgct gataagcgcg cccgcctcgc aaaaaccatc cctgatgaat    4380
ggaaagtcca gacgctgcct gcggaagaca gcgttattga tttcccaaag aaatcgggca    4440
tcctttcaga ggccgaactg aagatcacag aggcctccgc tgcagatctt gtgtccaagc    4500
tggcggccgg agagttgacc tcggtggaag ttacgctagc attctgtaaa cgggcagcaa    4560
tcgcccagca gttagtaggg tcccctctac ctctcaggga gatgtaacaa cgccaccta    4620 tgggactatc aagctgacgc tggcttctgt gcagacaaac tgcgcccacg agttcttccc    4680
tgacgccgct ctcgcgcagg caagggaact cgatgaatac tacgcaaagc acaagagacc    4740
cgttggtcca ctccatggcc tccccatctc tctcaaagac cagcttcgag tcaaggtaca    4800
ccgttgcccc taagtcgtta gatgtcccct tttgtcagct aacatatgcc accagggcta    4860
cgaaacatca atgggctaca tctcatggct aaacaagtac gacgaagggg actcggttct    4920
gacaaccatg ctccgcaaag ccggtgccgt cttctacgtc aagacctctg tcccgcagac    4980
cctgatggtc tgcgagacag tcaacaacat catcggcgcg accgtcaacc cacgcaacaa    5040
gaactggtcg tgcggcggca gttctggtgg tgagggtgcg atcgttggga ttcgtggtgg    5100
cgtcatcggt gtaggaacgg atatcggtgg ctcgattcga gtgccggccg cgttcaactt    5160
cctgtacggt ctaaggccga gtcatggcg gctgccgtat gcaaagatgg cgaacagcat    5220
ggagggtcag gagacggtgc acagcgttgt cgggccgatt acgcactctg ttgagggtga    5280
gtccttcgcc tcttccttct tttcctgctc tataccaggc ctccactgtc ctcctttctt    5340
gctttttata ctatatacga gaccggcagt cactgatgaa gtatgttaga cctccgcctc    5400
ttcaccaaat ccgtcctcgg tcaggagcca tggaaatacg actccaaggt catccccatg    5460
ccctggcgcc agtccgagtc ggacattatt gcctccaaga tcaagaacgg cgggctcaat    5520
atcggctact acaacttcga cggcaatgtc cttccacacc ctcctatcct gcgcggcgtg    5580
gaaaccaccg tcgccgcact cgccaaagcc ggtcacaccg tgaccccgtg gacgccatac    5640
aagcacgatt tcgccacga tctcatctcc catatctacg cggctgacgg cagcgccgac    5700
gtaatgcgcg atatcagtgc atccggcgag ccggcgattc caaatatcaa agacctactg    5760
aacccgaaca tcaagctgt taacatgaac gagctctggg acacgcatct ccagaagtgg    5820
aattaccaga tggagtacct tgagaaatgg cgggaggctg aagaaaaggc cgggaaggaa    5880
```

-continued

```
ctggacgcca tcatcgcgcc gattacgcct accgctgcgg tacggcatga ccagttccgg   5940
tactatgggt atgcctctgt gatcaacctg ctggatttca cgagcgtggt tgttccggtt   6000
acctttgcgg ataagaacat cgataagaag aatgagagtt tcaaggcggt tagtgagctt   6060
gatgccctcg tgcaggaaga gtatgatccg gaggcgtacc atggggcacc ggttgcagtg   6120
caggttatcg gacggagact cagtgaagag aggacgttgg cgattgcaga ggaagtgggg   6180
aagttgctgg gaaatgtggt gactccatag ctaataagtg tcagatagca atttgcacaa   6240
gaaatcaata ccagcaactg taaataagcg ctgaagtgac catgccatgc tacgaaagag   6300
cagaaaaaaa cctgccgtag aaccgaagag atatgacacg cttccatctc tcaaaggaag   6360
aatcccttca gggttgcgtt tccagtctag acgcgtcgcc ttgcggtgtg gttcttgtct   6420
ctgcgtccgg tttgtttgca tatcgtccct tggccactcc aaacccagcc caatcccgc    6480
ccaaactcgg tcttctcctc tttgtcccct gcccgagatg gttcttgctc ctctcttctg   6540
tctgtgtatc accacccact gacctcagca actccccccc cggggaggtt atgttgtatc   6600
atcaagccaa ttgttttgc tttgtttttt accccctcgt cccctcaacg tgcccctcca    6660
cggtgccctc catcgacggg ccgacggcat cggcgccgcc cgccggcgtg ctgccgccgc   6720
cttcggcctc ccactcctgc ggcgtctggc attttgcggt ccaggcgtgg atggcggcga   6780
tttcgtcctt gagggccgtg ttgacgaggc ggtgccgctt gagggccttg aggtcttgga   6840
actgggggga tacgatgagg gctgtgaagg cttggccgca gcctcctgtt tgacccggga   6900
agaaaacaca cataggttag cgacttttgg aggaggagtg tgtgcgttga gagaggaagg   6960
ggggggggg ggtttgtaga gggagtgatt tggttttggg aggaggagtt gtggataatg    7020
agggcggttt accggacatg tctgtgactt ggacgtggat tgcgccgagg cgctgggtga   7080
ttgcctcgcg gagggaggct tccgttattg aagccatttg aatggtggct atacagaggt   7140
gctctctgtt tgtttaggag ccctgtgtaa gagaagacgg gcgggtttcg caagaagtag   7200
tatgacaaat gtgatgttaa aagaatgatg gaaggtcgat ctgattgatt gattgattga   7260
ttgattagat agatcgtggg ggcgggacac acacacacac agtgcttaat cacacagttt   7320
tggtgcgtgt gtatgcacgg tatgagctca ttgggggaat ggggattggt ggagaggttg   7380
gaagaagaag aagaaagctt ggcttttagc ttgaggctga actgcataac tcagatcaag   7440
atcgaactta tctactactt tatttttacca tcagtttgat tctgtataag gtagttgacc   7500
aatctgcttt tgtctgcgtt ttgccctagg cagattgaca tgctactggc aagacgtctg   7560
ctagatagag gtcttcttct tccgtcggca cgcagagcag cagcagcagc agcagcagca   7620
gcgtctttgc gtcctgggtc ttcgcgcccg attcgcggtc ctcctcccct ccctcttcgc   7680
cctccatcgc gacagggcat ttctacgacg agccaacggc tcagcgacga cgacaagagc   7740
accagcgata tggctgaata cctggatggc gtgggcgctt ggggcgcgtg gcaggtacta   7800
gt                                                                 7802
```

<210> SEQ ID NO 16
<211> LENGTH: 3303
<212> TYPE: DNA
<213> ORGANISM: Artificial Sequence
<220> FEATURE:
<223> OTHER INFORMATION: Artificial DNA

<400> SEQUENCE: 16

```
ggtaccctga gagaacaggc agcatcttgc gagttctatg aggtgtctga taaaaaaaca    60
```

```
atacattact tatagacata ccactgccga caacttcatc tccatatcct ctgttccgtc    120
taactgattc gctcgctgtt ggatgatgac tcagcgtcgg ttggcctacg gtacatgtag    180
ggaggctgtc gagcaaccaa acccgcctgc taagctcatg cctggcctgt actgtatgaa    240
tccgcaacat aagctgcaac tcttcaaccc ctcgacagcc tgactcgcca ttccagaggc    300
cacgacacgc agccgttgct ggaggctctg ccgctagcga tttcctcgac agcctctgct    360
attccttctc ggctgtcctt ccaacaccgc tgttgtcgac tacactcgca gacgccttcg    420
aacacccgag acagcgtcac ccccagacac gggaccaaca ccttcgtgcc cctcctcctc    480
ctcctcctcc caccaactcc tcgacgatgg cggtgaatcg catccggggc gcctttgccg    540
cgcctcggaa gggagagaca ttcgagctgc gggccggcct ggtgtcgcag tatgcctacg    600
agcggaagga gtccatccag aagaccatca tggccatgac gctgggcaag gacgtgtccg    660
ccctgttccc agacgtcttg aagaacattg ccacgtccga cctggaccag aagaagctgg    720
tctacctcta cctcatgtat gtggctgcag acaatggccg accatgatca cacacacgga    780
gcgaaggacg agatactgcc tgacgtggcg atgcggtgct aacgtggagt gtgaccccag    840
gaactacgca aagacacacc cagacctctg cattctcgcc gtcaacacgt tcgtgcaaga    900
ctcggaagac ccgaacccgc tggtgcgagc gctggccatc cgcacaatgg gctgcatccg    960
ggtggacaag atggtcgact acatggagga gccgctgcgg aagacgctgc gggacgagtc   1020
gccgtacgtg cgcaagacgg ccgccatctg cgtggccaag ctgttcgacc tgaacccggc   1080
catgtgcatc gagaacggct tcatcgagac gctgcaggag atgattggcg acccgaaccc   1140
catggtggtc gcaaactcgg tccaggcgct ggccgagatt agcgagacgg cgcccgagac   1200
gcgggcgctg ctggtgacgc ccccggtgct caagaagctg cttatggcca tgaacgaatg   1260
caccgaatgg ggtagaatca ccattctgac cgtgctggca gactacgctg ccaccgacgt   1320
caaggagtcg gagcacatct gcgagagggt cattccgcag ttccagcacg tcaaccctag   1380
cgtggtcctg gctgctgtca aggtggtctt tattcatatg aagtcgatta acccggagct   1440
cgtgcggtca tatcttaaga agatggcgcc tccactcggt gcgttccgat catgtccccg   1500
atttgacatc tgagaagaca tgacgtgact atgctaacac tgcagcttgt atacagtcac   1560
actggttgct tctgccccg aggtcaaata cgtcgctctc agaaacattg atctgctcct   1620
tcaagccaag cccgacatcc tgagcaaaga gttaagagtc ttcttttgca aatacaacga   1680
cccgccgtac gtcaagatgc aaaagctgga atcatggtc aggatagcaa acgaaaagaa   1740
ctacgagcag ctcctgtctg agctcaagga atacgccctg gaagtggaca tggactttgt   1800
gcgccgagcc atcaaggcca tcggccaggt ggccatcaag attgaggagg ccagtggcaa   1860
gtgcgtgcag cgcgctggaa gatcttctcg ctaccaaggtc aactacgtgg tgcaagaggt   1920
tgtcgtggtc atcaaagata tcctgcgaaa gtaccccggt tacgagggcg tgatcccctc   1980
gctctgcaac tacattgacg agctcgacga ggccaatgct cgtggatccc tcatctggat   2040
tgtgggagag tacgccgaga agattagcaa cgctgaggag attctggagg ttttgtaga   2100 caccttttg gaggagttca ctcaggtatg tggagagctg tggaaaagtc ggggatttg   2160 gctaatcgaa ctgcagacac aactccagat ccttacagct gttgttaagc tgttttgaa   2220 gaagccgagt ggcgcgcagg gcctggttca gaaggtgctg caggaggcaa caaccaacaa   2280
cgacaacccc gatatccgcg acagagcata cgtctactgg cgattgttat cgggagattt   2340
ggaggtggcc aaggtaggag tcgttggcgt cctttgatga gagctgcgca tactgacgga   2400
tctcaagaac attgtcctgt cacagaagcc gaccatttca acaacaatga caagcctgcc   2460
```

```
gactgcgcta ctggagcagc tgctgtcgga gctgtcaact ctggcgtcgg tataccacaa    2520
gcccccggaa gcctttgtcg gcaagggccg gttcggtgcc gacgagatcc agcgagccgc    2580
catccaggag cagcgccaga acgccgcgga aaaccccatc gccgcatccg tggctgccgc    2640
cgccgccaat ggctcctcgt cggtctcgca aaacaacatt gagaacctgc tggacattga    2700 cttttgacggc gcagcaccgg cctctcagga gcagaacagc gcggcgggaa cacctgaccg    2760
ggtgtcgagc ccgccacggg gtggcatggc cgacatgatg agcatgtttg atgcgcctcc    2820
ggctggcagc tctggaggtg ctccgtccgg cggcatgaac gacttgatga acggatttga    2880
ggggctcaac tttggggcca cgagtacaaa tcagccgttg ccggcggcga tgcagctgca    2940
caatgcgcaa ggcggctctc agccgaagaa ggatagcgat gatcttttgg gtttgttgta    3000
aatgttggag gagcgtatat gcatgcaagc agcaagccag aaggggagaa gaatcgacaa    3060
gagagactgg aggaggaggc aagggagggg ggggttctt gggaggctgg aaaatatagt     3120
taataagtga tgcataggta tttgatgtcc tgtgagatat atacatgtta tgaagatata    3180
atttgagttg tctatacct tttagactttt tttcgagttg atgccagcag catcggcttc     3240
ggctcgtaag cgtttccact cgtcgtatct cttttgtttg atatccgtct tggcagcggc    3300
cgc                                                                  3303
```

<210> SEQ ID NO 17
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 17

```
atacgcgtcg ccttgcggtg tggttcttgt ctc                                   33
```

<210> SEQ ID NO 18
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 18

```
atactagtac ctgccacgcg ccccaagcgc cca                                   33
```

<210> SEQ ID NO 19
<211> LENGTH: 5778
<212> TYPE: DNA
<213> ORGANISM: Artificial Sequence.
<220> FEATURE:
<223> OTHER INFORMATION: DNA fragment for transformation

<400> SEQUENCE: 19

```
cttaagagtc ggaggttgga tgactaagtg cagaaagtga ggctcgtgaa ggtcctaaaa     60
tggaagcgct gcaggtggat gtggatcgtg ctctatgtgt gatactatac ctacttgact    120
tgctctttag caatgagtat tgcattgaat ctatactgag agaacaggca gcatcttgcg    180
agttctatga ggtgtctgat aaaaaaacaa tacattactt atagacatac cactgccgac    240
aacttcatct ccatatcctc tgttccgtct aactgattcg ctcgctgttg gatgatgact    300
cagcgtcggt tggcctacgg tacatgtagg gaggctgtcg agcaaccaaa cccgcctgct    360
aagctcatgc ctggcctgta ctgtatgaat ccgcaacata agctgcaact cttcaacccc    420
```

```
tcgacagcct gactcgccat tccagaggcc acgacacgca gccgttgctg gaggctctgc    480
cgctagcgat ttcctcgaca gcctctgcta ttccttctcg gctgtccttc aacaccgct    540 gttgtcgact acactcgcag acgccttcga acacccgaga cagcgtcacc cccagacacg    600
ggaccaacac cttcgtgccc ctcctcctcc tcctcctccc accaactcct cgacgatggc    660
ggtgaatcgc atccggggcg cctttgccgc gcctcggaag ggagagacat tcgagctgcg    720
ggccggcctg gtgtcgcagt atgcctacga gcggaaggag tccatccaga agaccatcat    780
ggccatgacg ctgggcaagg acgtgtccgc cctgttccca gacgtcttga agaacattgc    840
cacgtccgac ctggaccaga agaagctggt ctacctctac ctcatgtatg tggctgcaga    900
caatggccga ccatgatcac acacacggag cgaaggacga gatactgcct gacgtggcga    960
tgcggtgcta acgtggagtg tgaccccagg aactacgcaa agacacaccc agacctctgc    1020
attctcgccg tcaacacgtt cgtgcaagac tcggaagacc cgaacccgct ggtgcgagcg    1080
ctggccatcc gcacaatggg ctgcatccgg gtggacaaga tggtcgacta catggaggag    1140
ccgctgcgga agacgctgcg ggacgagtcg ccgtacgtgc gcaagacggc cgccatctgc    1200
gtggccaagc tgttcgacct gaacccggcc atgtgcatcg agaacggctt catcgagacg    1260
ctgcaggaga tgattggcga cccgaacccc atggtggtcg caaactcggt ccaggcgctg    1320
gccgagatta gcgagacggc gcccgagacg cgggcgctgc tggtgacgcc cccggtgctc    1380
aagaagctgc ttatggccat gaacgaatgc accgaatggg gtagaatcac cattctgacc    1440
gtgctggcgg ccgcctagtc atcattggat aggcagatta ctcagcctga atgacatcaa    1500
catgttaccc atgatacaat aggtcacaca aacaagcgct aagatgcact ggtatgaca    1560 agcccagtag tccgttttcaa aagacctaga tgatgaacta caacatgagg tgttgcctcc    1620
tgatccagtc caactgcaaa cgctgatgta tactcaatca agcctgatgt aaatgctgcg    1680
actcgattcg ctggatatga agatcaaaga gagctctgat gggtccaata tagccgggtt    1740
ttgttaggac agtccaccac accgatatta gaattggtca agcacctta catttcatag    1800 agattgcggt ttctagatct acgccaggac cgagcaagcc cagatgagaa ccgacgcaga    1860
tttccttggc acctgttgct tcagctgaat cctggcaata cgagatacct gctttgaata    1920
ttttgaatag ctcgcccgct ggagagcatc ctgaatgcaa gtaacaaccg tagaggctga    1980
cacggcaggt gttgctaggg agcgtcgtgt tctacaaggc cagacgtctt cgcggttgat    2040
atatatgtat gttttgactgc aggctgctca gcgacgacag tcaagttcgc cctcgctgct    2100
tgtgcaataa tcgcagtggg gaagccacac cgtgactccc atctttcagt aaagctctgt    2160
tggtgtttat cagcaataca cgtaatttaa actcgttagc atggggctga tagcttaatt    2220
accgtttacc agtgccgcgg ttctgcagct ttccttggcc cgtaaaattc ggcgaagcca    2280
gccaatcacc agctaggcac cagctaaacc ctataattag tctcttatca acaccatccg    2340
ctcccccggg atcaatgagg agaatgaggg ggatgcgggg ctaaagaagc ctacataacc    2400
ctcatgccaa ctcccagttt acactcgtcg agccaacatc ctgactataa gctaacacag    2460
aatgcctcaa tcctgggaag aactggccgc tgataagcgc gcccgcctcg caaaaccat    2520 ccctgatgaa tggaaagtcc agacgctgcc tgcggaagac agcgttattg atttcccaaa    2580
gaaatcgggc atcctttcag aggccgaact gaagatcaca gaggcctccg ctgcagatct    2640
tgtgtccaag ctggcggccg gagagttgac ctcggtggaa gttacgctag cattctgtaa    2700
acgggcagca atcgcccagc agttagtagg gtcccctcta cctctcaggg agatgtaaca    2760
acgccacctt atgggactat caagctgacg ctggcttctg tgcagacaaa ctgcgcccac    2820
```

```
gagttcttcc ctgacgccgc tctcgcgcag gcaagggaac tcgatgaata ctacgcaaag   2880
cacaagagac ccgttggtcc actccatggc ctccccatct ctctcaaaga ccagcttcga   2940
gtcaaggtac accgttgccc ctaagtcgtt agatgtccct ttttgtcagc taacatatgc   3000
caccagggct acgaaacatc aatgggctac atctcatggc taaacaagta cgacgaaggg   3060
gactcggttc tgacaaccat gctccgcaaa gccggtgccg tcttctacgt caagacctct   3120
gtcccgcaga ccctgatggt ctgcgagaca gtcaacaaca tcatcgggcg caccgtcaac   3180
ccacgcaaca agaactggtc gtgcggcggc agttctggtg gtgagggtgc gatcgttggg   3240
attcgtggtg gcgtcatcgg tgtaggaacg gatatcggtg gctcgattcg agtgccggcc   3300
gcgttcaact tcctgtacgg tctaaggccg agtcatgggc ggctgccgta tgcaaagatg   3360
gcgaacagca tggagggtca ggagacggtg cacagcgttg tcgggccgat tacgcactct   3420
gttgagggtg agtccttcgc ctcttccttc ttttcctgct ctataccagg cctccactgt   3480
cctcctttct tgcttttat actatatacg agaccggcag tcactgatga agtatgttag    3540
acctccgcct cttcaccaaa tccgtcctcg gtcaggagcc atggaaatac gactccaagg   3600
tcatccccat gccctggcgc cagtccgagt cggacattat tgcctccaag atcaagaacg   3660
gcgggctcaa tatcggctac tacaacttcg acggcaatgt ccttccacac cctcctatcc   3720
tgcgcggcgt ggaaaccacc gtcgccgcac tcgccaaagc cggtcacacc gtgaccccgt   3780
ggacgccata caagcacgat ttcggccacg atctcatctc ccatatctac gcggctgacg   3840
gcagcgccga cgtaatgcgc gatatcagtg catccggcga gccggcgatt ccaaatatca   3900
aagacctact gaacccgaac atcaaagctg ttaacatgaa cgagctctgg gacacgcatc   3960
tccagaagtg gaattaccag atggagtacc ttgagaaatg gcgggaggct gaagaaaagg   4020
ccgggaagga actggacgcc atcatcgcgc cgattacgcc taccgctgcg gtacggcatg   4080
accagttccg gtactatggg tatgcctctg tgatcaacct gctggatttc acgagcgtgg   4140
ttgttccggt tacctttgcg gataagaaca tcgataagaa gaatgagagt ttcaaggcgg   4200
ttagtgagct tgatgccctc gtgcaggaag agtatgatcc ggaggcgtac catggggcac   4260
cggttgcagt gcaggttatc ggacggagac tcagtgaaga ggacgttg gcgattgcag    4320 aggaagtggg gaagttgctg ggaaatgtgg tgactccata gctaataagt gtcagatagc   4380
aatttgcaca agaaatcaat accagcaact gtaaataagc gctgaagtga ccatgccatg   4440
ctacgaaaga gcagaaaaaa acctgccgta gaaccgaaga gatatgacac gcttccatct   4500
ctcaaaggaa gaatcccttc agggttgcgt ttccagtcta cacgcgtgag tacgccgaga   4560
agattagcaa cgctgaggag attctggagg gttttgtaga caccttttg gaggagttca    4620 ctcaggtatg tggagagctg tggaaaagtc ggggattttg gctaatcgaa ctgcagacac   4680
aactccagat ccttacagct gttgttaagc tgtttttgaa gaagccgagt ggcgcgcagg   4740
gcctggttca gaaggtgctg caggaggcaa caaccaacaa cgacaacccc gatatccgcg   4800
acagagcata cgtctactgg cgattgttat cgggagattt ggaggtggcc aaggtaggag   4860
tcgttggcgt cctttgatga gagctgcgca tactgacgga tctcaagaac attgtcctgt   4920
cacagaagcc gaccatttca acaacaatga caagcctgcc gactgcgcta ctggagcagc   4980
tgctgtcgga gctgtcaact ctggcgtcgg tataccacaa gccccggaa gcctttgtcg     5040 gcaagggccg gttcggtgcc gacgagatcc agcgagccgc catccaggag cagcgccaga   5100
acgccgcgga aaacccatc gccgcatccg tggctgccgc cgccgccaat ggctcctcgt     5160
```

```
cggtctcgca aaacaacatt gagaacctgc tggacattga ctttgacggc gcagcaccgg    5220
cctctcagga gcagaacagc gcggcgggaa caccectgaccg ggtgtcgagc ccggccacgg   5280
gtggcatggc cgacatgatg agcatgtttg atgcgcctcc ggctggcagc tctggaggtg    5340
ctccgtccgg cggcatgaac gacttgatga acggatttga ggggctcaac tttggggcca    5400
cgagtacaaa tcagccgttg ccggcggcga tgcagctgca caatgcgcaa ggcggctctc    5460
agccgaagaa ggatagcgat gatcttttgg gtttgttgta aatgttggag gagcgtatat    5520
gcatgcaagc agcaagccag aaggggagaa gaatcgacaa gagagactgg aggaggaggc    5580
aagggagggg gggggttctt gggaggctgg aaaatatagt taataagtga tgcataggta    5640
tttgatgtcc tgtgagatat atacatgtta tgaagatata atttgagttg tctatacccct   5700 tttagacttt tttcgagttg atgccagcag catcggcttc ggctcgtaag cgtttccact    5760
cgtcgtatct ctactagt                                                  5778

<210> SEQ ID NO 20
<211> LENGTH: 36
<212> TYPE: DNA
<213> ORGANISM: Artificial Sequence
<220> FEATURE:
<223> OTHER INFORMATION: Oligo DNA for PCR

<400> SEQUENCE: 20
atgcatctta agagtcggag gttggatgac taagtg                              36

<210> SEQ ID NO 21
<211> LENGTH: 35
<212> TYPE: DNA
<213> ORGANISM: Artificial Sequence
<220> FEATURE:
<223> OTHER INFORMATION: Oligo DNA for PCR

<400> SEQUENCE: 21
atgcggccgc cagcacggtc agaatggtga ttcta                               35

<210> SEQ ID NO 22
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 22
atacgcgtga gtacgccgag aagattagca acg                                 33

<210> SEQ ID NO 23
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 23
atactagtag agatacgacg agtggaaacg ctt                                 33
```

MUTANT OF *TRICHODERMA* FILAMENTOUS FUNGUS AND METHOD OF PRODUCING PROTEIN

TECHNICAL FIELD

This disclosure relates to a mutant strain of a filamentous fungus of the genus *Trichoderma*, the mutant strain being capable of keeping a viscosity of a culture solution low, and to a method of protein production using the mutant strain.

BACKGROUND

Filamentous fungi of the genus *Trichoderma* are known to have a high protein-producing ability, and studies have heretofore been made on protein production using filamentous fungi of the genus *Trichoderma*. Specifically, filamentous fungi of the genus *Trichoderma* are used especially to produce a cellulase, which is classified as a saccharifying enzyme, among proteins using cellulose, lactose, cellobiose or the like as an inducer. To enhance the cellulase production amount, various investigations have hitherto been made such as genetic modifications including overexpression or deletion of a factor that controls cellulase production and optimization of cultivation conditions.

Meanwhile, filamentous fungi of the genus *Trichoderma* belong to the aerobic filamentous fungi, which essentially require oxygen for growth and protein production. Filamentous fungi of the genus *Trichoderma* are characterized in that when the filamentous fungi are cultivated in a liquid culture medium, the viscosity of the culture solution increases as the filamentous fungi grow. The increase in culture solution viscosity results in an uneven distribution of oxygen and nutrients. Hence, it is necessary in cultivating a filamentous fungus of the genus *Trichoderma* to stir the culture solution or increase the oxygen feed rate to thereby prevent the degree of saturation of oxygen dissolved in the culture solution from decreasing and keep the degree of saturation at or above a certain level. Meanwhile, use of a cultivation tank having a larger size results in a decrease in oxygen-transfer coefficient. Hence, it is necessary to keep the degree of saturation of oxygen dissolved in the culture solution at or above a certain level, to further increase the number of stirring or oxygen feed rate. However, increasing the number of stirring poses a problem in that the fungus bodies suffer considerable shear damage, while increasing the oxygen feed rate poses a problem in that a larger amount of energy is necessary.

JP-T-2013-533751, JP-T-2014-513529, JP-T-2014-513530, JP-T-2014-513531, JP-T2014-513532 and JP-T-2014-513533 disclose that when the Sfb3, Mpg1, Gas1, Seb1, Crz1, and Tps1 proteins of a filamentous fungus of the genus *Trichoderma* are destroyed or are reduced in protein production, the mutant strains can be cultivated by aerobic fermentation in submerged culture while maintaining a dissolved-oxygen concentration with a small number of stirring, as compared with their parent strains. WO 2017/170917 indicates that by destroying a BXL1 gene of a filamentous fungus of the gnus *Trichoderma*, the culture solution can be inhibited from decreasing in the degree of saturation of dissolved oxygen.

As described above, it is exceedingly important in producing a protein using a filamentous fungus of the genus *Trichoderma* to inhibit the dissolved-oxygen concentration in the culture solution from decreasing and keep the concentration thereof at or above a certain level. It is thought that in producing a protein by liquid-medium cultivation of a filamentous fungus of the genus *Trichoderma*, if the viscosity of the culture solution can be kept low, not only the energy required for stirring can be reduced but also the degree of saturation of oxygen dissolved in the culture solution can be inhibited from decreasing, even when using an enlarged cultivation scale.

It could therefore be helpful to provide a mutant strain of a filamentous fungus of the genus *Trichoderma* that renders the viscosity of the culture solution low and provide a method of protein production using the mutant strain of a filamentous fungus of the genus *Trichoderma*.

SUMMARY

We discovered that a mutation of a beta-adaptin large subunit makes it possible to keep the viscosity of the culture solution low and inhibit the degree of saturation of oxygen dissolved in the culture solution from decreasing. We thus provide:

(1) A mutant strain of a filamentous fungus of the genus *Trichoderma*, the mutant strain having a mutation that deletes or reduces a function of a beta-adaptin large subunit,
in which a culture solution of the mutant strain has a lower viscosity than a culture solution of a parent strain having no mutation that deletes or reduces the function of the beta-adaptin large subunit.

(2) A mutant strain of a filamentous fungus of the genus *Trichoderma*, the mutant strain having a mutation in an amino acid sequence constituting a beta-adaptin large subunit,
in which a culture solution of the mutant strain has a lower viscosity than a culture solution of a parent strain having no mutation in the amino acid sequence constituting the beta-adaptin large subunit.

(3) The mutant strain of a filamentous fungus of the genus *Trichoderma* according to (2), in which the mutation in the amino acid sequence is a mutation in which a glutamine residue that is the 300th residue from the N-terminal side of the amino acid sequence constituting the beta-adaptin large subunit has been changed to an amino acid residue other than glutamine.

(4) The mutant strain of a filamentous fungus of the genus *Trichoderma* according to (3), in which the amino acid residue other than glutamine is lysine.

(5) The mutant strain of a filamentous fungus of the genus *Trichoderma* according to any one of (1) to (4), in which the amino acid sequence constituting the beta-adaptin large subunit is any of the amino acid sequences represented by SEQ ID NOs: 2 to 10.

(6) The mutant strain of a filamentous fungus of the genus *Trichoderma* according to any one of (1) to (5), in which the filamentous fungus of the genus *Trichoderma* is *Trichoderma reesei*.

(7) A method of producing a protein, the method including a step of cultivating the mutant strain of a filamentous fungus of the genus *Trichoderma* according to any one of (1) to (6).

(8) A method of producing a cellulase, the method including a step of cultivating the mutant strain of a filamentous fungus of the genus *Trichoderma* according to any one of (1) to (6).

Our mutant strain of a filamentous fungus of the genus *Trichoderma* not only enables the culture solution to retain a lower viscosity than the parent strain before introduction of the mutation but also can inhibit the culture solution from decreasing in the degree of saturation of dissolved oxygen.

Furthermore, this mutant strain has an unexpected effect that a protein, in particular a cellulase, is produced in an improved amount.

BRIEF DESCRIPTION OF THE DRAWINGS

FIG. 1A shows a comparison among the overall amino acid sequences constituting beta-adaptin large subunits possessed by filamentous fungi of the genus *Trichoderma*. The amino acid sequence identified as *Trichoderma reesei* corresponds to SEQ ID NO. 2, the amino acid sequence identified as *Trichoderma citrinoviride* corresponds to SEQ ID NO: 3, the amino acid sequence identified as *Trichoderma longibrachiatum* corresponds to SEQ ID NO: 4, the amino acid sequence identified as *Trichoderma vixens* corresponds to SEQ ID NO: 5, the amino acid sequence identified as *Trichoderma atroviride* corresponds to SEQ ID NO: 6, the amino acid sequence identified as *Trichoderma gamsii* corresponds to SEQ ID NO. 7, the amino acid sequence identified as *Trichoderma asperellum* corresponds to SEQ ID NO: 8, the amino acid sequence identified as *Trichoderma harzianum* corresponds to SEQ ID NO: 9, and the amino acid sequence identified as *Trichoderma guizhouense* corresponds to SEQ ID NO: 10.

FIG. 1B shows a comparison among the overall amino acid sequences constituting the beta-adaptin large subunits possessed by the filamentous fungi of the genus *Trichoderma*. The amino acid sequence identified as *Trichoderma reesei* corresponds to SEQ ID NO. 2, the amino acid sequence identified as *Trichoderma citrinoviride* corresponds to SEQ ID NO: 3, the amino acid sequence identified as *Trichoderma longibrachiatum* corresponds to SEQ ID NO: 4, the amino acid sequence identified as *Trichoderma vixens* corresponds to SEQ ID NO: 5, the amino acid sequence identified as *Trichoderma atroviride* corresponds to SEQ ID NO: 6, the amino acid sequence identified as *Trichoderma gamsii* corresponds to SEQ ID NO: 7, the amino acid sequence identified as *Trichoderma asperellum* corresponds to SEQ ID NO: 8, the amino acid sequence identified as *Trichoderma harziamun* corresponds to SEQ ID NO: 9, and the amino acid sequence identified as *Trichoderma guizhouense* corresponds to SEQ ID NO: 10.

DETAILED DESCRIPTION

Figure 2:
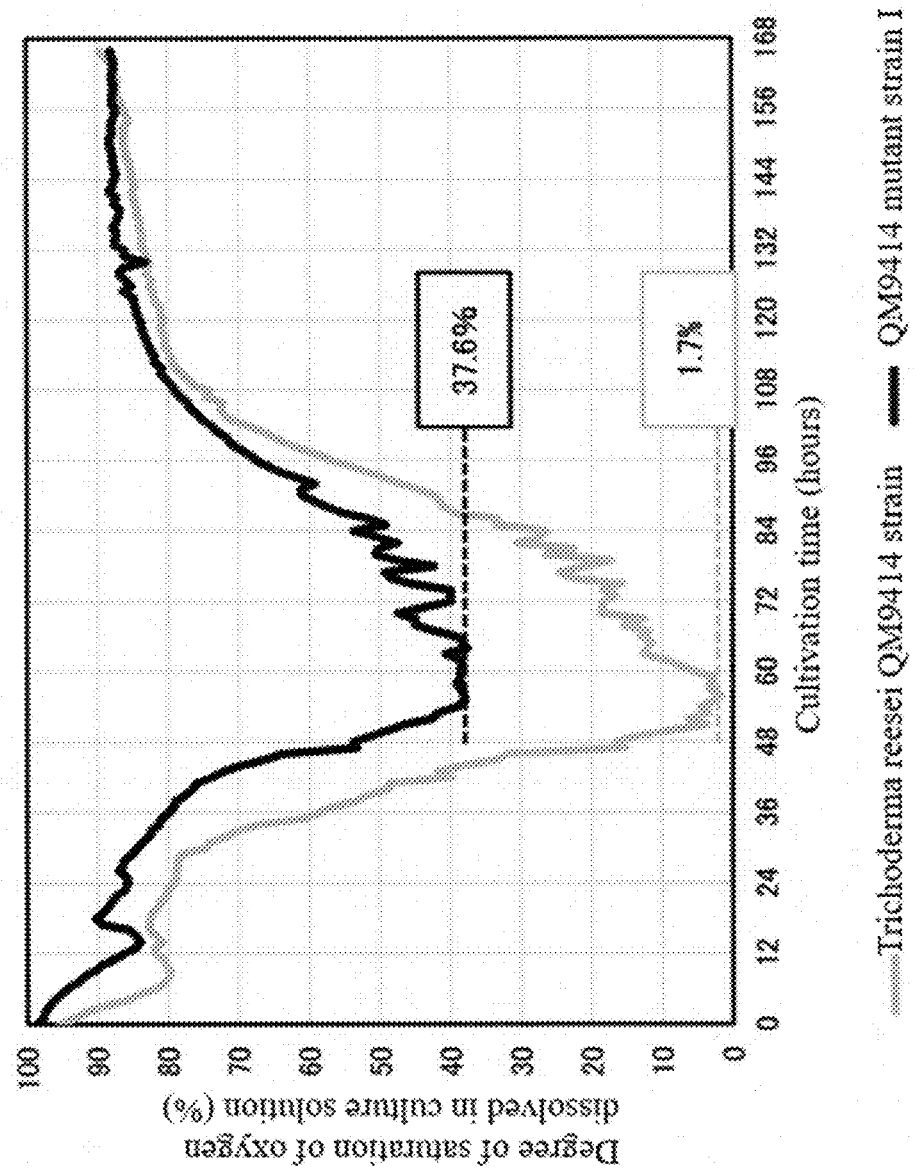
FIG. 2 shows changes with the lapse of time of the degree of saturation of oxygen dissolved in culture solutions in cultivation of a *Trichoderma reesei* QM9414 strain and QM9414 mutant strain I with Arbocel B800.

Our fungi are characterized in that a mutation is introduced into a parent strain of a filamentous fungus of the genus *Trichoderma*, which is a microorganism originally having an excellent protein-producing ability, to thereby enable the mutant strain to be cultivated in a culture solution retaining a low viscosity. The parent strain of a filamentous fungus of the genus *Trichoderma* is not limited to wild strains, and mutant strains of a filamentous fungus of the genus *Trichoderma* that have been improved to have an increased protein-producing ability can also be favorably used as the parent strain. For example, a mutant strain having an improved protein production property obtained by performing a mutation treatment with a mutagen, UV irradiation or the like can be utilized as the parent strain of a mutant strain of a filamentous fungus of the genus *Trichoderma*.

Specific examples of the parent strain include *Trichoderma parareesei* (ATCC MYA4777), which is an ancestor to *Trichoderma reesei*, and the following known mutant strains belonging to *Trichoderma reesei*: QM6a strain (NBRC31326), QM9123 strain (ATCC24449), QM9414 strain (NBRC31329), PC-3-7 strain (ATCC66589), QM9123 strain (NBRC31327), RutC-30 strain (ATCC56765), CL-847 strain (*Enzyme. Microbiol. Technol.*, 10, 341-346 (1998)), MCG77 strain (*Biotechnol. Bioeng. Symp.*, 8, 89 (1978)), MCG80 strain (*Biotechnol. Bioeng.*, 12, 451-459 (1982)), *Trichoderma citrinoviride* (ATCC24961), *Trichoderma longibrachiatum* (ATCC18648), *Trichoderma virens* (ATCC9645), *Trichoderma atroviride* (ATCC20476), *Trichoderma gamsii* (NFCCI2177), *Trichoderma asperellum* (ATCC52438), *Trichoderma harzianum* (ATCC20846), and *Trichoderma guizhouense*. QM6a strain, QM9419 strain, and QM9123 strain are available from NBRC (NITE Biological Resource Center), PC-3-7 strain, RutC-30 strain, *Trichoderma citrinoviride*, *Trichoderma longibrachiatum*, *Trichoderma virens*, *Trichoderma atroviride*, *Trichoderma asperellum*, and *Trichoderma harzianum* are available from ATCC (American Type Culture Collection), and *Trichoderma gamsii* is available from NFCCI (National Fungal Culture Collection of India). Among these examples, especially preferred strains for use as the parent strain are the strains belonging to *Trichoderma reesei*.

A beta-adaptin large subunit is one of the proteins constituting an adaptor protein complex, which is a tetramer. Adaptor protein complexes are widely conserved in eucaryotes. The adaptor proteins are known to bind to clathrin to constitute vesicles which take part in transport inside and outside the cells and inside and outside the fungus bodies (*Proc. Nati. Acad. Sci. USA.*, 101, 14108-14113 (2004)).

Figure 1A:
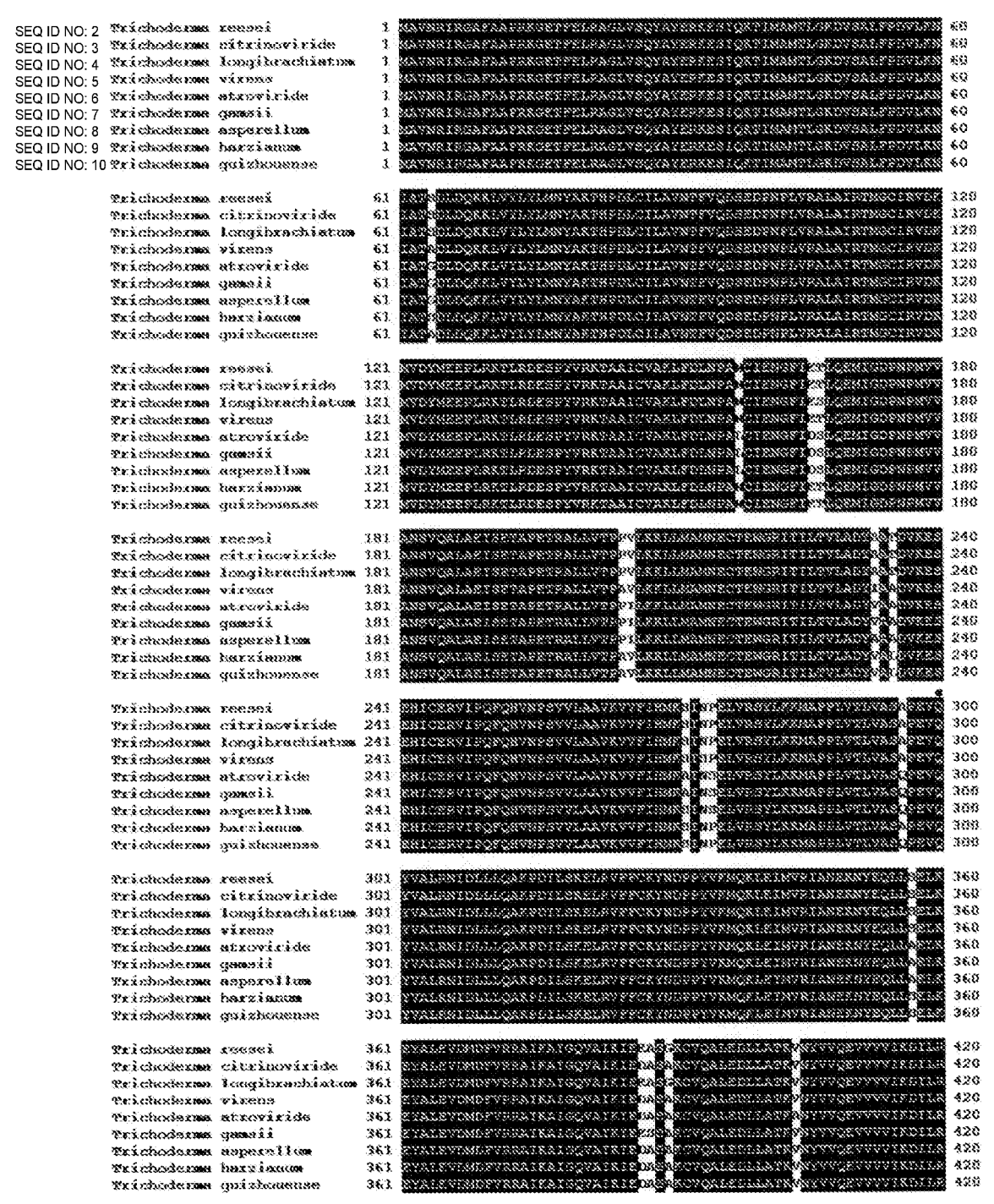
Figure 1B:
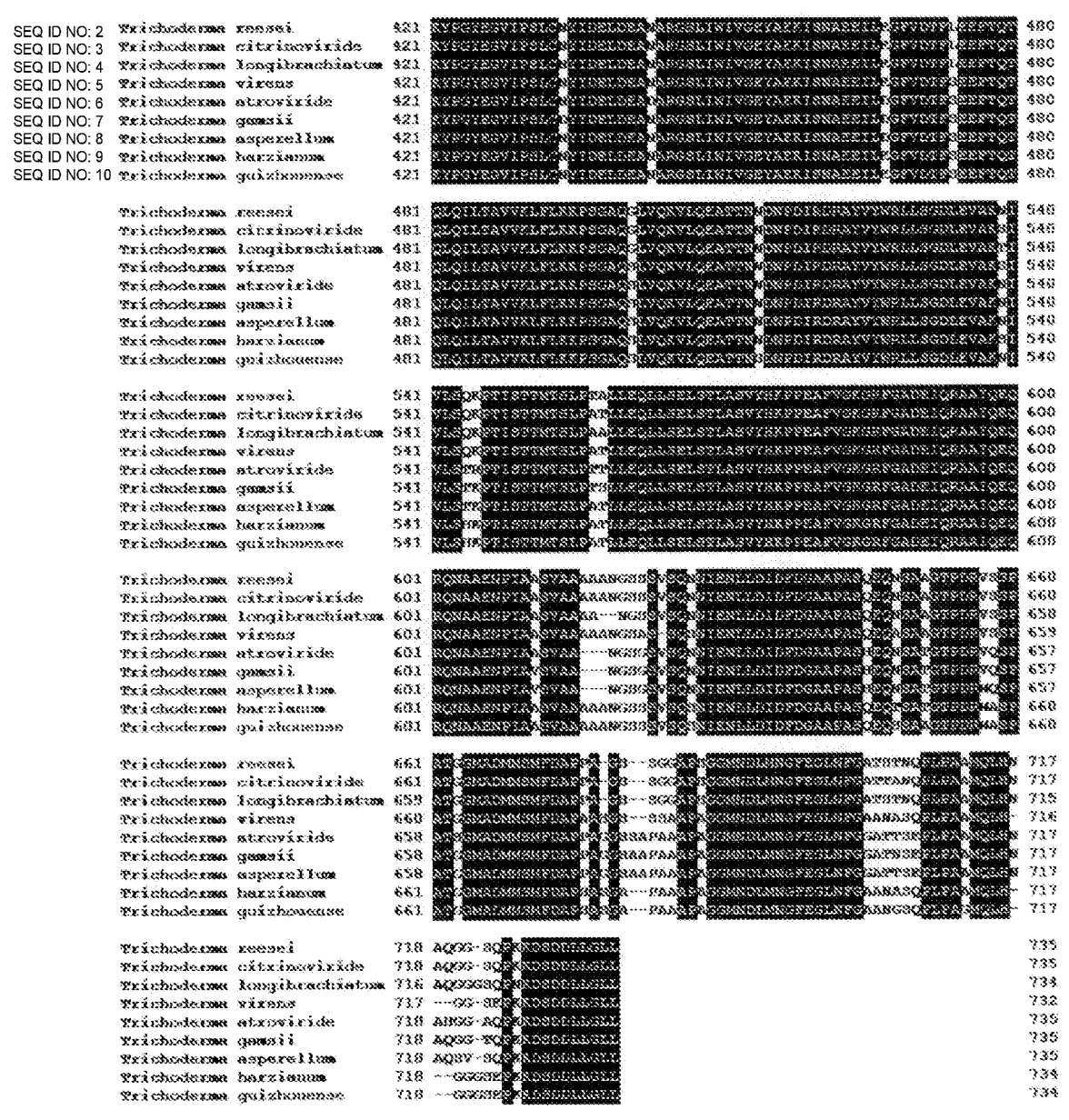

A preferred example of the beta-adaptin large subunits possessed by filamentous fungi of the genus *Trichoderma* is the polypeptide consisting of an amino acid sequence represented by any of SEQ ID NOs: 2 to 10. The amino acid sequence represented by SEQ ID NO: 2 is derived from *Trichoderma reesei*, the amino acid sequence represented by SEQ ID NO: 3 is derived from *Trichoderma citrinoviride*, the amino acid sequence represented by SEQ ID NO: 4 is derived from *Trichoderma longibrachiatum*, the amino acid sequence represented by SEQ ID NO: 5 is derived from *Trichoderma virens*, the amino acid sequence represented by SEQ ID NO: 6 is derived from *Trichoderma atroviride*, the amino acid sequence represented by SEQ ID NO: 7 is derived from *Trichoderma gamsii*, the amino acid sequence represented by SEQ ID NO: 8 is derived from *Trichoderma asperellum*, the amino acid sequence represented by SEQ ID NO: 9 is derived from *Trichoderma harzianum*, and the amino acid sequence represented by SEQ ID NO: 10 is derived from *Trichoderma guizhouense*. The results of an alignment of the amino acid sequences represented by SEQ ID NOs: 2 to 10 are shown in FIGS. 1A and 1B. As FIGS. 1A and 1B show, the sequence identity for the SEQ ID NOs: 2 to 10 is 90% or higher, indicating that the beta-adaptin large subunits in the filamentous fungus of the genus *Trichoderma* have a high degree of amino acid sequence conservation. Furthermore, as FIG. 1A shows, in the amino acid sequences represented by SEQ ID NOs: 2 to 10, a glutamine residue is conserved in common as the 300th amino acid residue from the N-terminal side. Features thereof are further explained below using SEQ ID NO: 2 as an example.

The polypeptide consisting of the amino acid sequence represented by SEQ ID NO: 2 is a polypeptide possessed by *Trichoderma reesei*, as stated above, and has been registered at National Center for Biotechnology Information as adaptor protein (AP-1) complex beta-adaptin large subunit (EGR48910) possessed by *Trichoderma reesei* QM6a strain. Meanwhile, Conserved Domain Architecture Retrieval Tool of National Center for Biotechnology Information discloses that the 14th to 531th amino acid residues from the N-terminal side have an adaptin N terminal region domain.

A mutation in the amino acid sequence constituting a beta-adaptin large subunit may be any of the deletion, substitution, and addition of an amino acid. It is preferable that the mutation is one in which the glutamine residue that is the 300th amino acid residue from the N-terminal side in the amino acid sequence represented by any of SEQ ID NOs: 2 to 10 has been changed to an amino acid residue other than glutamine. Especially preferred is a mutation in which the glutamine residue has been changed to lysine.

Specific examples of genes encoding the polypeptide consisting of the amino acid sequence represented by SEQ ID NO: 2 include the base sequence represented by SEQ ID NO: 1.

Specific examples of base sequences encoding the amino acid sequence obtained from the amino acid sequence represented by SEQ ID NO: 2 by changing the glutamine residue which is the 300th residue from the N-terminal side into an amino acid residue other than glutamine include the base sequence represented by SEQ ID NO: 1 in which the cytosine as the 1,080th base has been changed to adenine. This mutation results in a mutation in which the 300th amino acid residue from the N-terminal side in the amino acid sequence represented by SEQ ID NO: 2 is changed from glutamine to lysine.

Our mutant strain of a filamentous fungus of the genus *Trichoderma* may be a mutant strain in which a function of a beta-adaptin large subunit has been deleted or reduced.

The phrase "a function of a beta-adaptin large subunit is deleted or reduced" means a total or partial loss of the polypeptide, a change of the whole or some of the polypeptide into different amino acid(s), or a combination of these. More specifically, that phrase means that the amino acid sequence represented by SEQ ID NO: 2 comes to have a sequence identity of 80% or less, with respect to the amino acid sequence of the beta-adaptin large subunit described above. The sequence identity thereto is preferably 50% or less, more preferably 20% or less, more preferably 10% or less, more preferably 5% or less, more preferably 3% or less, more preferably 1% or less, and most preferably 0%. Examples of methods for the total or partial deletion of the beta-adaptin large subunit or the total or partial change thereof into different amino acid(s) include a method in which a gene sequence encoding the polypeptide consisting of the amino acid sequence represented by SEQ ID NO: 2 is caused to undergo a frame shift or stop codon mutation due to base deletion, insertion, substitution and the like.

Examples of the reduction of a function of a beta-adaptin large subunit include a total or partial deletion of the beta-adaptin large subunit. It is also possible to reduce a function of the beta-adaptin large subunit by introducing a mutation which diminishes or inhibits the expression of the beta-adaptin large subunit. The diminution or inhibition of the expression of the beta-adaptin large subunit is attained by causing a mutation to the promoter or terminator region of a gene encoding the beta-adaptin large subunit. In general, the promoter and terminator regions correspond to a region of hundreds of bases in length before and after the gene participating in transcription. It is known that when the amino acid sequence itself constituting a beta-adaptin large subunit has not undergone a mutation such as an amino acid deletion, substitution, or addition, a function of the protein is reduced by a mutation such as an amino acid deletion, substitution, or addition, caused to an amino acid sequence lying outside the beta-adaptin large subunit. It is also known that even when the gene itself encoding a beta-adaptin large subunit has not undergone a mutation such as a base deletion, substitution, or addition, a function of the protein is reduced by a mutation such as a base deletion, substitution, or addition, caused to a base sequence lying outside the gene encoding the beta-adaptin large subunit.

To introduce such mutations that delete or reduce a function of the beta-adaptin large subunit or for introducing such a mutation into the amino acid sequence constituting the beta-adaptin large subunit, use can be made of known genetic mutation methods such as a mutation treatment with a mutagen known to those skilled in the art or with UV irradiation or the like, gene recombination such as homologous recombination using a selection marker, and a mutation by a transposon.

Our mutant strain of a filamentous fungus of the genus *Trichoderma* is lower in the viscosity of the culture solution and is more effective in inhibiting the degree of saturation of oxygen dissolved in the culture solution from decreasing compared to the parent strain into which the mutation has not been introduced. Thus, the energy necessary for aeration and stirring and rotation frequency can be reduced. Furthermore, since the rotation frequency of stirring can be set low, the shearing damage to the fungus bodies can be reduced. This mutant strain is more effective in large-scale cultivation because reductions in the capacity of the blower and stirring motor necessary for aeration and in stirring energy are attained.

The viscosity of a culture solution is a value measured under the following conditions, and culture solutions are compared in viscosity by comparing maximum ones of the values measured under the following conditions. First, spores of the mutant strain of a filamentous fungus of the genus *Trichoderma* and the parent strain that are to be evaluated are inoculated into preculture media (a specific example of culture compositions is as shown in Table 1 given in the Examples) to result in a concentration of $1.0 \times 10^5$ spores per mL of the preculture medium, and cultivation is conducted on a shaker under the conditions of 28° C. and 120 rpm until the amount of fungus bodies becomes around 11 g/L. Next, each of the preculture media is inoculated, in an amount of 10% (v/v), into a main-culture medium shown in Table 2, to which celluose fiber (ARBOCEL® B 800) (manufactured by J. Rettenmaier & Sohne) has been added in an amount of 100 g/L (w/v), and submerged culture is conducted using a 5-L jar fermenter. Specifically, after inoculation of the preculture medium into the main-culture medium, submerged culture is conducted under the conditions of 28° C., 700 rpm, and an air flow rate of 100 mL/min while regulating the pH to 5.0. To measure the viscosity of the culture medium, a digital rotational viscometer is used. The digital rotational viscometer is subjected to zero point calibration beforehand. At 39, 48, 62, 72, 86, 96, and 111 hours after initiation of the cultivation, the culture solution is sampled and a 16-mL portion of each sample is immediately introduced into a given vessel. A spindle is immersed in the culture solution and rotated at a rotational speed of 0.3 rpm to measure the resultant torque, which is the viscosity resistance imposed on the spindle, at room temperature, thereby measuring the viscosity of the culture solution. The unit of the viscosity is centipoise (cP). One poise is defined as the viscosity of a fluid which, when having therein a velocity gradient of 1 cm/sec per cm, has a stress of 1 dyne per $cm^2$ along the direction of the flow in a plane perpendicular to the direction of the velocity gradient. As the digital rotational viscometer, for example, DV2T (BROOKFIELD Inc.) can be used. As the spindle, for example, UL ADAPTOR (BROOKFIELD Inc.) can be used.

Our mutant strain of a filamentous fungus of the genus *Trichoderma* is lower in the viscosity of the culture solution as compared with the parent strain into which the mutation has not been introduced when the two strains are cultivated under the same conditions. The maximum viscosity during the cultivation thereof is lower by preferably 100 cP or larger, more preferably 200 cP or larger, more preferably 400 cP or larger, more preferably 500 cP or larger, still more preferably 600 cP or larger, still more preferably 700 cP or larger, still more preferably 800 cP or larger, still more preferably 900 cP or larger, especially preferably 1,000 cP or larger.

The degree of saturation of oxygen dissolved in the culture solution can be calculated by measuring the rate of oxygen utilization in the culture solution. The term "rate of oxygen utilization (mM/L/hr)" means oxygen consumption rate per L of the culture solution per unit time period measured at 24 hours after cultivation initiation. A specific method for the calculation is as follows. Cultivation is conducted under constant cultivation conditions and the feeding of oxygen is stopped at 24 hours after initiation of the cultivation. Values of dissolved-oxygen concentration (mg/L) (DO values) determined at intervals of 10 seconds are plotted and, then, in the resultant curve, three or more plotted points which decline logarithmically are examined for slope (A) (unit; DO/sec). Expression (1) is used to calculate the rate of oxygen utilization:

$$\text{Rate of oxygen utilization(mM/L/hr)} = (-A) \times (1/32) \times 60 \times 60 \quad (1).$$

To measure the DO values, a commercial DO meter can be used. The DO meter to be used is not particularly limited, and any DO meter capable of accurately measuring the DO values may be used. Examples thereof include sealed DO electrodes (manufactured by ABLE Corp.) and a dissolved-oxygen sensor (manufactured by Mettler-Toledo International Inc.). The DO meter is subjected beforehand to zero point calibration and span calibration. The zero point calibration is performed using a 2% solution of sodium sulfite. The span calibration is performed by conducting aeration and stirring under the same conditions as in actual cultivation except for the absence of fungal bodies, waiting until the culture solution becomes saturated with dissolved oxygen, thereafter ascertaining that the meter stably indicates a value, and calibrating the value to the saturation concentration of dissolved oxygen at the temperature. When the cultivation tank is pressurized in measuring DO values, it is necessary to perform a pressure correction. Furthermore, when the cultivation tank is large, it is necessary to perform a hydrostatic-pressure correction. In performing the correction, Expression (2) is used for calculation:

$$D = DO(1+\alpha+\beta) \quad (2)$$

D: corrected saturation concentration of dissolved oxygen
DO: saturation concentration of dissolved oxygen in pure water at 1 atm
α: gage pressure ($kg/cm^2$)
β: hydrostatic pressure [(depth (m) of liquid at the position of DO meter)/10].

The degree of saturation of dissolved oxygen is determined by calculating the proportion of the dissolved-oxygen concentration during the cultivation to a saturation concentration of dissolved oxygen in the fungus-free culture medium that has been brought into a dissolved-oxygen-saturated state by blowing air thereinto under the same pH and temperature conditions as in the cultivation, the saturation concentration of dissolved oxygen being taken as 100%. The dissolved-oxygen concentration (mg/L) is the concentration of oxygen dissolved in the water. The term "saturation concentration of dissolved oxygen" means the dissolved-oxygen concentration in a culture medium which, in the state of containing no fungus bodies, has been made to have a constant dissolved-oxygen concentration by performing aeration and stirring under the same cultivation conditions as in actual cultivation. In calculating the degree of saturation of dissolved oxygen, the cultivation conditions including aeration conditions are kept unchanged throughout the cultivation period. A decrease in oxygen demand results in an increase in the degree of saturation of dissolved oxygen. The degree of saturation of dissolved oxygen is calculated in accordance with Expression (3):

$$\text{Degree of saturation of dissolved oxygen (\%)} = \text{(dissolved-oxygen concentration during cultivation)} / \text{(saturation concentration of dissolved oxygen before cultivation initiation)} \times 100 \quad (3).$$

In comparing degrees of saturation of dissolved oxygen, minimum values are compared to each other.

When rates of oxygen utilization or degrees of saturation of dissolved oxygen are compared, use is made of results measured through examinations conducted under the same cultivation conditions including culture medium, oxygen feed rate, stirring speed, temperature, cultivation volume, and inoculation amount. The inoculation amount in the examinations is preferably about 10% (v/v) with respect to the main-culture solution.

When the mutant strain of a filamentous fungus of the genus *Trichoderma* and the parent strain into which the mutation has not been introduced are cultivated under the same dissolved-oxygen conditions, the mutant strain gives a higher minimum value of the degree of saturation of dissolved oxygen than the parent strain. The minimum value thereof is higher by preferably 5% or larger, more preferably 6% or larger, more preferably 7% or larger, more preferably 8% or larger, more preferably 9% or larger, more preferably 10% or larger, more preferably 11% or larger, more preferably 12% or larger, more preferably 13% or larger, more preferably 14% or larger, especially preferably 15% or larger.

It is preferable that the mutant strain of a filamentous fungus of the genus *Trichoderma* does not have a lower growing ability than the parent strain into which the mutation has not been introduced. A difference in growing ability can be determined by measuring the amounts of fungus bodies. The amount of fungus bodies is measured as the weight of dry fungus bodies. A 10-mL portion of the culture solution is subjected to suction filtration using a qualitative filter paper (Grade 4; GE Healthcare Co.), and the residue is dried at 100° C. together with the filter paper. The weight thereof is measured and a difference of filter-paper weight between before and after the filtration is taken as the weight of the dry fungus bodies.

Our mutant strain of a filamentous fungus of the genus *Trichoderma* may have a genetic mutation that improves protein production amount, besides having a mutation which deletes or reduces a function of a beta-adaptin large subunit or a mutation of the amino acid sequence constituting a beta-adaptin large subunit. Specific examples thereof include a genetic mutation which reduces a function of the polypeptide(s) represented by SEQ ID NO: 11 and/or SEQ ID NO: 13.

The polypeptide consisting of the amino acid sequence represented by SEQ ID NO: 11 is a polypeptide possessed by *Trichoderma reesei* and has been registered at National Center for Biotechnology Information as predicted protein EGR50654 possessed by *Trichoderma reesei* QM6a strain. The polypeptide consisting of the amino acid sequence represented by SEQ ID NO: 11 is a polypeptide whose function is unknown, but Conserved Domain Architecture Retrieval Tool of National Center for Biotechnology Information discloses that the 95th to 277th amino acid residues from the N-terminal side have middle domain of eukaryotic initiation factor 4G domain (hereinafter referred to as MIF4G domain) and the 380th to 485th amino acid residues from the N-terminal side have MA-3 domain. The two domains, MIF4G and MA-3, are known to have the function of binding to DNAs or RNAs (*Biochem.*, 44, 12265-12272 (2005); *Mol. Cell. Biol.*, 1, 147-156 (2007)). It is presumed from those disclosures that the polypeptide consisting of the amino acid sequence represented by SEQ ID NO: 11 at least has the function of binding to a DNA and/or an RNA.

Specific examples of genes encoding the polypeptide consisting of the amino acid sequence represented by SEQ ID NO: 11 include the base sequence represented by SEQ ID NO: 12. Examples of genetic mutations which reduce the function of EGR50654 include a total deletion of the MIF4G domain and/or MA-3 domain possessed by EGR50654, a partial deletion of the MIF4G domain and/or MA-3 domain, and a genetic mutation which changes the configuration relationship between the MIF4G domain and the MA-3 domain. Furthermore, the function of the polypeptide consisting of the amino acid sequence represented by SEQ ID NO: 11 can be reduced also by introducing a mutation that diminishes or inhibits the expression of the polypeptide. Specific examples of the deletion of the function of the polypeptide consisting of the amino acid sequence represented by SEQ ID NO: 11 include a mutation in the base sequence represented by SEQ ID NO: 12 which deletes any of the 1,039th to 1,044th bases.

The polypeptide consisting of the amino acid sequence represented by SEQ ID NO: 13 is a polypeptide possessed by *Trichoderma reesei* and has been registered at National Center for Biotechnology Information as predicted protein EGR44419 possessed by *Trichoderma reesei* QM6a strain. The polypeptide consisting of the amino acid sequence represented by SEQ ID NO: 13 is a polypeptide whose function is unknown, but Conserved Domain Architecture Retrieval Tool of National Center for Biotechnology Information discloses that the 26th to 499th amino acid residues from the N-terminal side have a sugar (and other) transporter domain. It is presumed from this disclosure that the polypeptide consisting of the amino acid sequence represented by SEQ ID NO: 13 at least participates in transport of sugar between the inside and the outside of the fungus bodies.

Specific examples of genes encoding the polypeptide consisting of the amino acid sequence represented by SEQ ID NO: 13 include the base sequence represented by SEQ ID NO: 14. Examples of genetic mutations that reduce the function of EGR44419 include a total deletion of the sugar (and other) transporter domain possessed by EGR44419, a partial deletion of the sugar (and other) transporter domain, and a genetic mutation that changes the configuration relationship of the sugar (and other) transporter domain. Furthermore, the function of the polypeptide consisting of the amino acid sequence represented by SEQ ID NO: 13 can be reduced also by introducing a mutation that diminishes or inhibits the expression of the polypeptide. Specific examples of the deletion of the function of the polypeptide consisting of the amino acid sequence represented by SEQ ID NO: 13 include a mutation in the base sequence represented by SEQ ID NO: 14 which inserts eleven bases at the 1,415th position.

We further provide a method of protein production including a step of cultivating the mutant strain of a filamentous fungus belonging to the genus *Trichoderma* in which an amino acid sequence constituting a beta-adaptin large subunit has a mutation.

Our method can efficiently produce proteins excreted from the fungus bodies. The proteins to be produced are not limited, but enzymes are preferred. More preferred are saccharifying enzymes such as cellulases, amylases, invertases, chitinases, and pectinases. Especially preferred are cellulases.

Cellulases that can be produced include various hydrolases that include enzymes having a decomposition activity against xylan, cellulose, and hemicellulose. Specific examples thereof include cellobiohydrolase (EC 3.2.1.91) that produces cellobiose by hydrolyzing cellulose chains, endoglucanase (EC 3.2.1.4) that hydrolyzes cellulose chains from central portions thereof, β-glucosidase (EC 3.2.1.21) that hydrolyzes cellooligosaccharide and cellobiose, xylanase (EC 3.2.1.8) that is characterized by acting on hemicellulose and, in particular, on xylan, and β-xylosidase (EC 3.2.1.37) that hydrolyzes xylooligosaccharide.

The concentration of a cellulase protein is determined in the following manner. A culture solution obtained by cultivating a filamentous fungus of the genus *Trichoderma* by our method is centrifuged at 15,000×g for 10 minutes and the resultant supernatant is recovered as a cellulase solution. To 250 µL of protein concentration assay (QUICK START™ Bradford Protein Assay (manufactured by Bio-Rad Laboratories, Inc.) is added 5 µL of the cellulase solution which has been diluted. This mixture is allowed to stand at room temperature for 15 minutes and then examined for absorbance at 595 nm. The concentration of the protein contained in the saccharifying-enzyme solution is calculated on the basis of a calibration curve obtained using bovine serum albumin solutions as reference solutions.

Methods of cultivating a filamentous fungus of the genus *Trichoderma* are not particularly limited. For example, the strain can be cultivated by liquid culture using a centrifuge tube, flask, jar fermenter, tank, or the like or solid culture using a plate or the like. It is preferred to cultivate the filamentous fungus of the genus *Trichoderma* under aerobic conditions, and especially preferred of those cultivation methods is submerged culture performed in a jar fermenter or a tank while conducting aeration or stirring.

The culture medium composition in the cultivating step is not particularly limited as long as it is a culture medium composition where the filamentous fungus of the genus *Trichoderma* can produce a protein, and a known culture medium composition for microbes of the genus *Trichoderma* can be employed. As a nitrogen source, use can be made, for example, of polypeptone, bouillon, CSL, or soybean cake. An inducer for protein production may be added to the culture medium.

In producing cellulases, the mutant strain can be cultivated in a culture medium containing one or more inducers selected from the group consisting of lactose, cellulose, and xylan. For introducing cellulose or xylan, biomass containing cellulose or xylan may be added as an inducer. Specific examples of the biomass containing cellulose or xylan include not only plants such as seed plant, pteridophyte, bryophyte, algae, and water plant, but also waste building materials. The seed plants are classified into gymnosperms and angiosperms, and both can be used favorably. The angiosperms are further classified into monocotyledons and dicotyledons. Specific examples of the monocotyledons include bagasse, switchgrass, napier grass, erianthus, corn stover, corncob, rice straw, and wheat straw, and specific examples of the dicotyledons include beet pulp, *eucalyptus*, oak, and white birch.

As for the biomass containing cellulose or xylan, a pretreated product may be used. The pretreatment method is not particularly limited, but, for example, known methods such as acid treatment, sulfuric acid treatment, dilute sulfuric acid treatment, alkali treatment, hydrothermal treatment, subcritical treatment, fine grinding treatment, and steaming treatment can be used. Pulp may be used as such a pretreated biomass containing cellulose or xylan.

Methods of cultivating the mutant strain of a filamentous fungus of the genus *Trichoderma* are not particularly limited. For example, the mutant strain can be cultivated by liquid culture using a centrifuge tube, flask, jar fermenter, tank, or the like or solid culture using a plate or the like. When the mutant strain is a mutant strain of *Trichoderma reesei*, it is preferred to cultivate this mutant strain under aerobic conditions, and especially preferred is submerged culture performed in a jar fermenter or a tank while conducting aeration or stirring. The air flow rate is preferably about 0.1-2.0 vvm, more preferably 0.3-1.5 vvm, especially preferably 0.5-1.0 vvm. The cultivation temperature is preferably about 25-35° C., more preferably 25-31° C. The pH conditions during the cultivation are preferably pH 3.0-7.0, more preferably pH 4.0-6.0. The cultivation period is not particularly limited so long as the cultivation can be conducted under conditions capable of protein production, until the protein is accumulated in a recoverable amount. However, the cultivation period is usually 24-288 hours, preferably 24-240 hours, more preferably 36-240 hours, still more preferably 36-192 hours.

Methods of recovering a protein contained in the culture solution where the mutant strain of a filamentous fungus of the genus *Trichoderma* has been cultivated are not particularly limited, but the protein can be recovered by removing the bodies of the filamentous fungus of the genus *Trichoderma* from the culture solution. Examples of methods of removing the fungus bodies include centrifugation, membrane separation, and filter press.

Furthermore, when the culture solution in which the mutant strain of the filamentous fungus of the genus *Trichoderma* has been cultivated is used as a protein solution without removing the fungus bodies therefrom, the culture solution is preferably treated so that the fungus bodies of the filamentous fungus of the genus *Trichoderma* cannot grow therein. Examples of treatment methods of preventing the fungus bodies from growing include heat treatment, chemical treatment, acid/alkali treatment, and UV treatment.

When the protein is an enzyme such as a cellulase, the culture solution from which the fungus bodies have been removed or which has been treated so that the fungus bodies cannot grow, as stated above, can be used directly as an enzyme solution.

EXAMPLES

Our fungi and methods are described specifically below by referring to Examples.

Reference Example 1: Method of Measuring Protein Concentration

A protein concentration measurement reagent protein concentration assay (QUICK START™ Bradford Protein Assay, produced by Bio-Rad Laboratories, Inc.) was used. 5 µL of a diluted filamentous fungus culture solution was added to 250 µL of the protein concentration measurement reagent returned to room temperature. After leaving the mixture to stand at room temperature for 5 minutes, the absorbance at 595 nm was measured using a microplate reader. Using BSA as a standard, the protein concentration was calculated based on the calibration curve.

Reference Example 2: Calculation of Degree of Saturation of Dissolved Oxygen

The degree of saturation of dissolved oxygen was determined by calculating the proportion of the dissolved-oxygen concentration during the cultivation to a saturation concentration of dissolved oxygen in the fungus-free culture medium that had been brought into a dissolved-oxygen-saturated state by blowing air thereinto under the same pH and temperature conditions as in the cultivation, the saturation concentration of dissolved oxygen being taken as 100%. As a DO meter, sealed dissolved-oxygen electrode SDOC-12F-L120 (manufactured by ABLE Corp.) was used.

Reference Example 3: Measurement of Viscosity of Culture Solution

Culture solution samples collected at 39, 48, 62, 72, 86, 96, and 111 hours after initiation of cultivation were examined for viscosity (cP) using digital rotational viscometer DV2T and spindle UL ADAPTOR (manufactured by BROOKFIELD Inc.) at a rotational speed set at 0.3 rpm.

Reference Example 4: Measurement of Amount of Fungus Bodies

The amount of fungus bodies contained in a culture solution was determined by subjecting the culture solution to suction filtration with a filter paper and taking the difference in the weight of the filter paper with dry fungus bodies between before and after the suction filtration as the amount of the fungus bodies.

Example 1

Preparing of *Trichoderma reesei* QM9414 Mutant Strain I Reduced in the Function of Beta-Adaptin Large Subunit A DNA fragment consisting of the gene sequence represented by SEQ ID NO: 15 was prepared as a DNA fragment including a gene encoding the polypeptide consisting of the amino acid sequence represented by SEQ ID NO: 2 in which the amino acid sequence constituting a beta-adaptin large subunit had a mutation. This DNA fragment was used to transform *Trichoderma reesei* QM9414 strain. Thus, a mutant strain of *Trichoderma reesei* reduced in the function of the beta-adaptin large subunit was prepared. By this method, a *Trichoderma reesei* mutant strain is obtained in which the cytosine as the 1,080th residue in SEQ ID NO: 1 has been replaced by adenine to have a polypeptide in which the 300th residue in SEQ ID NO: 2 has been changed from glutamine to lysine. Acetamide and acetamidase (AmdS) gene (amdS) capable of decomposing acetamide were used as selection markers for introducing the DNA fragment. To allow the DNA fragment consisting of the base sequence represented by SEQ ID NO: 15 to be introduced upstream and downstream the amdS-containing DNA sequence, a plasmid for mutation introduction was prepared to add a portion homologous to the gene sequence of the *Trichoderma reesei* QM9414 strain.

Specifically, a DNA fragment obtained by treating a synthesized DNA fragment shown by SEQ ID NO: 16 with restriction enzymes KpnI and NotI was used as the upstream DNA fragment. In addition, PCR was conducted using genomic DNA extracted in a usually manner from the *Trichoderma reesei* QM9414 strain and oligo DNAs represented by SEQ ID NOs: 17 and 18, and the resulting amplified fragment was treated with restriction enzymes MluI and SpeI to obtain a DNA fragment, which was used as the downstream DNA fragment. The upstream and downstream DNA fragments were introduced into an amdS-containing plasmid by using restriction enzymes KpnI and NotI and restriction enzymes MluI and SpeI, respectively, to construct a plasmid for mutation introduction. The plasmid for mutation introduction was treated with restriction enzymes ApaI and AscI, and the *Trichoderma reesei* QM9414 strain (NBRC31329) was transformed with the obtained DNA fragment shown by SEQ ID NO: 15. The obtained mutant strain was used as QM9414 mutant strain I in the following experiments.

The manipulations involving the molecular biological technique were performed as described in Molecular cloning, laboratory manual, 1st, 2nd, 3rd (1989). In addition, the transformation was carried out using a standard technique, i.e., a protoplast PEG method, and specifically, was performed as described in Gene, 61, 165-176 (1987).

Example 2

Protein Production Test Using QM9414 Mutant Strain I

Preculture

After spores of QM9414 mutant strain I prepared in Example 1 were diluted with physiological saline to be $1.0 \times 10^7$/mL, 2.5 mL of the diluted spore solution was inoculated into 250 mL of the preculture medium shown in Table 1 that had been placed in a 1-L baffled flask, and was incubated on a shaker under the conditions of 28° C. and 120 rpm for 72 hours.

TABLE 1

| | |
|---|---|
| Glucose | 20 g |
| 5 × Mandel's solution* | 200 mL |
| 10 × Ammonium tartrate solution** | 100 mL |
| Corn steep liquor | 50 g |
| Trace element solution*** | 1 mL |
| Tween 80 | 0.5 mL |
| PE-M | 1 mL |
| | (per 1 L) |

TABLE 1-continued

*The 5 × Mandel's solution has the following composition:
7 g/L (NH$_4$)$_2$SO$_4$
10 g/L KH$_2$PO$_4$
2 g/L CaCl$_2$ · 2H$_2$O
1.5 g/L MgSO$_4$ · 7H$_2$O.
**The 10 × Ammonium tartrate solution contains 92 g/L ammonium tartrate.
***The trace element solution has the following composition:
0.3 g/L H$_3$BO$_3$
1.3 g/L (NH$_4$)$_6$Mo$_7$O$_{24}$ · 4H$_2$O
5 g/L FeCl$_3$ · 6H$_2$O
2 g/L CuSO$_4$ · 5H$_2$O
0.4 g/L MnCl$_2$ · 4H$_2$O
10 g/L ZnCl$_2$.

Main Culture

Cellulose fiber ARBOCEL® B 800) (J. Rettenmaier & Sohne) was added to the main-culture medium shown in Table 2, and an investigation of submerged culture was conducted using a 5-L jar fermenter (manufactured by ABLE & Biott Co., Ltd.). The preculture solutions of the *Trichoderma reesei* QM9414 strain and the QM9414 mutant strain I prepared in Example 1 were each inoculated in an amount of 250 mL into 2.5 L of the main-culture medium to which cellulose fiber (ARBOCEL® B 800) had been added. After the inoculation of each preculture medium into the main-culture medium, submerged culture was performed under the cultivation conditions of 28° C., 700 rpm, and an air flow rate of 100 mL/min while regulating the pH to 5.0.

TABLE 2

| Arbocel B800 cellulose fiber (ARBOCEL ® B 800) (produced by J. Rettenmaier & Sohne) 100 g | |
|---|---|
| 5 × Mandel's solution* | 200 mL |
| Corn steep liquor | 25 g |
| Trace element solution*** | 1 mL |
| Tween 80 | 0.5 mL |
| PE-M | 1 mL |
| | (per 1 L) |

*Same as in Table 1.
***Same as in Table 1.

Sampling of Culture Solution

At each of 39, 48, 62, 72, 86, 96, and 111 hours after initiation of the cultivation, a 20-mL portion of the culture solution was collected. A portion of the collected culture solution was centrifuged under the conditions of 15,000×g and 4° C. for 10 minutes to obtain a supernatant. The supernatant was filtered with a 0.22-μm filter, and the filtrate was used as a cellulase solution in the following experiments.

Measurement of Protein Concentration

The cellulase protein concentration in each culture solution collected at 96 hours after initiation of the cultivation was determined using the technique described in Reference Example 1. As a result, QM9414 mutant strain I gave a protein concentration of 1.3 times higher in relative value than the protein concentration obtained with the *Trichoderma reesei* QM9414 strain.

Measurement of Degree of Saturation of Oxygen Dissolved in Culture Solution

Using the technique described in Reference Example 2, the degree of saturation of oxygen dissolved in each culture solution was determined over the lapse of time. As a result, as FIG. 2 shows, the degree of saturation of oxygen dissolved in the culture solution of the *Trichoderma reesei* QM9414 strain had decreased to a minimum value of 1.7% at about 60 hours after initiation of the cultivation, whereas the degree of saturation of oxygen dissolved in the culture solution of QM9414 mutant strain I had a minimum value of 37.6%.

Measurement of Viscosity of Culture Solution

Figure 3:
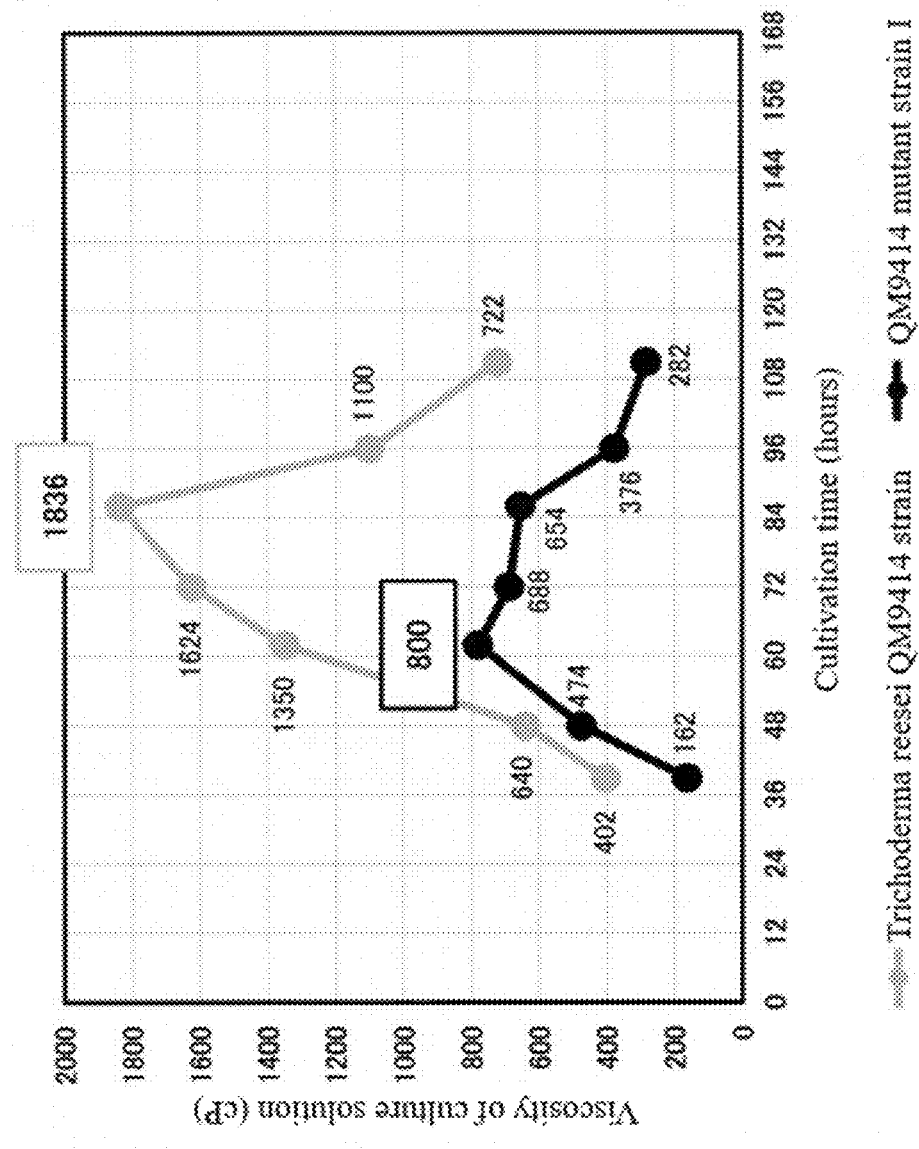
FIG. 3 shows changes with the lapse of time of the viscosity of the culture solutions in the cultivation of a *Trichoderma reesei* QM9414 strain and QM9414 mutant strain I with Arbocel B800.

Using the technique described in Reference Example 3, the viscosity of each culture solution was measured over the lapse of time. As a result, as FIG. 3 shows, the culture solution of the *Trichoderma reesei* QM9414 strain had a maximum viscosity of 1,800 cP or higher, whereas the culture solution of the *Trichoderma reesei* mutant strain had a maximum viscosity of 800 cP or less. We found results that QM9414 mutant strain I enables the culture solution to retain a low viscosity and to be inhibited from decreasing in the degree of saturation of dissolved oxygen.

Measurement of Amount of Fungus Bodies

Using the technique described in Reference Example 4, the amount of fungus bodies contained in each culture solution collected at 72 hours after initiation of the cultivation in Example 2 (Preculture) was measured. As a result, the amount of the fungus bodies of the *Trichoderma reesei* QM9414 strain was 11.3 g/L, and the amount of the fungus bodies of QM9414 mutant strain I was 11.0 g/L. No difference in fungus body amount was observed between the two strains.

Example 3

Preparation of *Trichoderma reesei* QM9414 Mutant Strain II Reduced in the Function of Beta-Adaptin Large Subunit A mutant strain of *Trichoderma reesei* reduced in the function of the beta-adaptin large subunit was prepared by preparing a DNA fragment consisting of the gene sequence represented by SEQ ID NO: 19 and using this DNA fragment to transform *Trichoderma reesei* QM9414 strain. By this method, amdS is inserted between the 791th and 792th residues in SEQ ID NO: 1 to obtain a mutant strain of *Trichoderma reesei* reduced in the function of the beta-adaptin large subunit. To introduce the DNA fragment consisting of the SEQ ID NO: 19, a plasmid for mutation introduction was prepared to add a portion homologous to the gene sequence of the *Trichoderma reesei* QM9414 strain upstream and downstream the amdS-containing DNA fragment sequence.

Specifically, PCR was conducted using genomic DNA extracted in a usual manner from the *Trichoderma reesei* QM9414 strain and oligo DNAs expressed by SEQ ID NOs: 20 and 21, and the resulting amplified fragment was treated with restriction enzymes AflII and NotI to obtain a DNA fragment that was used as the upstream fragment. In addition, PCR was conducted using the genomic DNA and oligo DNAs expressed by SEQ ID NOs: 22 and 23, and the resulting amplified fragment was treated with restriction enzymes MluI and SpeI to obtain a DNA fragment, which was used as the downstream fragment. The upstream and downstream DNA fragments were introduced into an amdS-containing plasmid by using restriction enzymes AflII and NotI and restriction enzymes MluI and SpeI, respectively, to construct a plasmid for mutation introduction. The plasmid for mutation introduction was treated with restriction enzymes AflII and SpeI, and the *Trichoderma reesei* QM9414 strain was transformed with the obtained DNA fragment shown by SEQ ID NO: 19, in the same manner as in Example 1. The obtained *Trichoderma reesei* mutant strain was used as QM9414 mutant strain II in the following experiments.

Example 4

Protein Production Test Using QM9414 Mutant Strain II

Cultivation was conducted by the same operation under the same conditions as in Example 2, except that QM9414 mutant strain II was used in place of the QM9414 mutant strain I prepared in Example 1. The concentration of a protein contained in the culture solution, the degree of saturation of oxygen dissolved in the culture solution, and the viscosity of the culture solution were measured in the same manner as in Example 2.

Measurement of Protein Concentration

When the protein concentration in the culture solution obtained by cultivating the *Trichoderma reesei* QM9414 strain was taken as 1, the relative value of the protein concentration in the culture solution of QM9414 mutant strain II was 1.4. We found that the *Trichoderma reesei* reduced in the function of the beta-adaptin large subunit can produce a protein in an improved amount when cultivated as compared to when the protein function has not been reduced.

Measurement of Degree of Saturation of Oxygen Dissolved in Culture Solution

Figure 4:
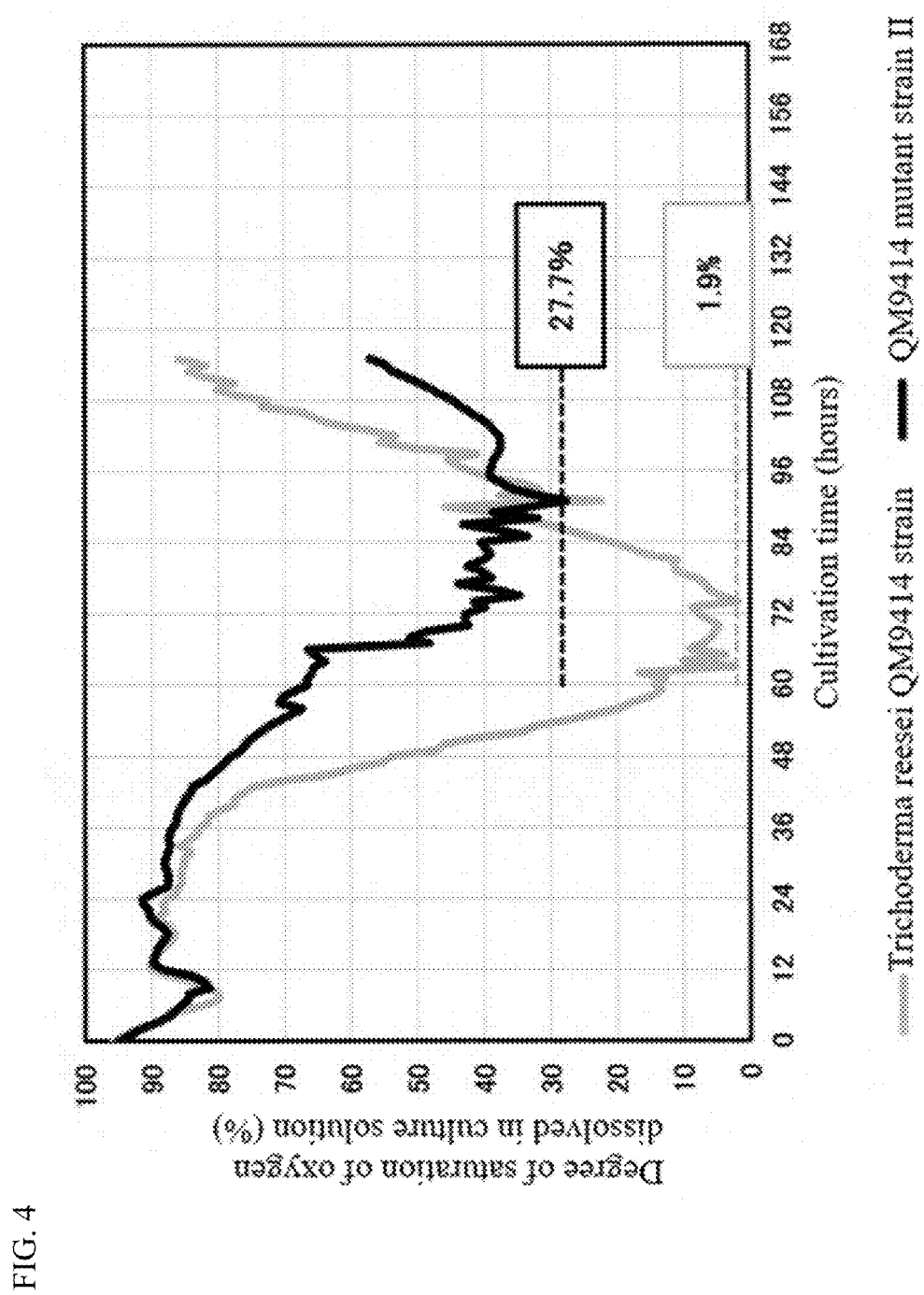
FIG. 4 shows changes with the lapse of time of the degree of saturation of oxygen dissolved in culture solutions in cultivation of a *Trichoderma reesei* QM9414 strain and QM9414 mutant strain II with Arbocel B800.

Using the technique described in Reference Example 2, the degree of saturation of oxygen dissolved in each culture solution was determined over the lapse of time. As a result, as FIG. 4 shows, the degree of saturation of oxygen dissolved in the culture solution of the *Trichoderma reesei* QM9414 strain had decreased to a minimum value of 1.9% at about 60 hours after initiation of the cultivation, whereas the degree of saturation of oxygen dissolved in the culture solution of QM9414 mutant strain II had a minimum value of 27.7%.

Measurement of Viscosity of Culture Solution

Figure 5:
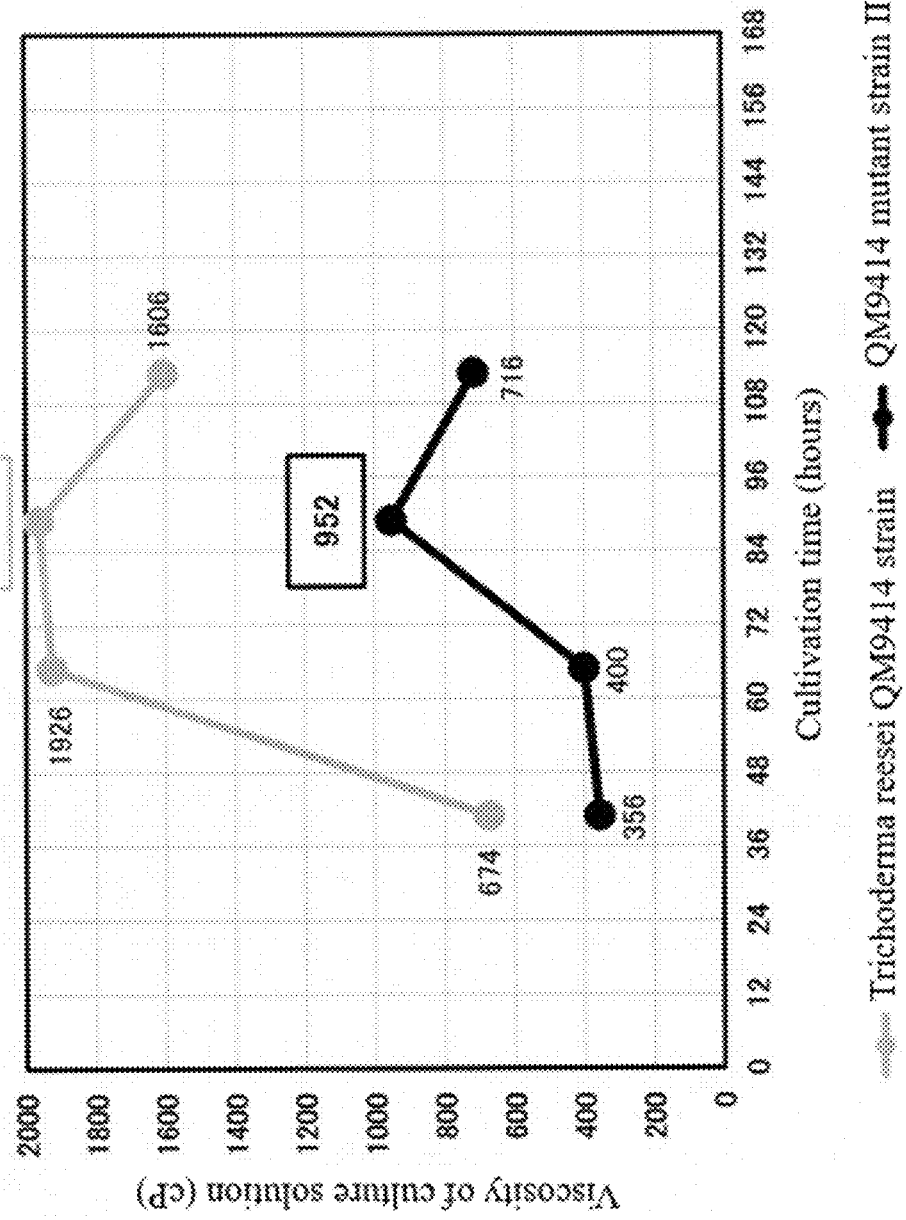
FIG. 5 shows changes with the lapse of time of the viscosity of the culture solutions in the cultivation of a *Trichoderma reesei* QM9414 strain and QM9414 mutant strain II with Arbocel B800.

Using the technique described in Reference Example 3, the viscosity of each culture solution was measured over the lapse of time. As a result, as FIG. 5 shows, the culture solution of the *Trichoderma reesei* QM9414 strain had a maximum viscosity of 1,900 cP or higher, whereas the culture solution of the QM9414 mutant strain II had a maximum viscosity of 1,000 cP or less. We found that QM9414 mutant strain II enables the culture solution to retain a low viscosity and to be inhibited from decreasing in the degree of saturation of dissolved oxygen.

The invention claimed is:

1. A mutant strain of a filamentous fungus of the genus *Trichoderma*, the mutant strain having a mutation that eliminates expression of a beta-adaptin large subunit,
wherein a culture solution of the mutant strain has a lower viscosity than a culture solution of a parent strain having no mutation that eliminates the function of the beta-adaptin large subunit and the mutant strain does not have a lower growing ability than the parent strain,
wherein the amino acid sequence constituting the beta-adaptin large subunit of the parent strain has 90% or more sequence identity with SEQ ID NO:2, and
wherein the mutation is a total deletion of the beta-adaptin large subunit.

2. The mutant strain of a filamentous fungus of the genus *Trichoderma* according to claim 1, wherein the amino acid sequence constituting the beta-adaptin large subunit is any of the amino acid sequences represented by SEQ ID NOs: 2 to 10.

3. The mutant strain of a filamentous fungus of the genus *Trichoderma* according to claim 1, wherein the filamentous fungus of the genus *Trichoderma* is *Trichoderma* reesei.

4. A method of producing a protein, the method comprising a step of cultivating the mutant strain of a filamentous fungus of the genus *Trichoderma* according to claim 1.

5. A method of producing a cellulase, the method comprising a step of cultivating the mutant strain of a filamentous fungus of the genus *Trichoderma* according to claim 1.

6. A mutant strain of a filamentous fungus of the genus *Trichoderma*, the mutant strain having a mutation in an amino acid sequence constituting a beta-adaptin large subunit, wherein a culture solution of the mutant strain has a lower viscosity than a culture solution of a parent strain having no mutation in the amino acid sequence constituting the beta-adaptin large subunit and the mutant strain does not have a lower growing ability than the parent strain, and wherein the mutation in the amino acid sequence is a mutation in which a glutamine residue that is the 300th residue from the N-terminal side of the amino acid sequence constituting the beta-adaptin large subunit has been changed to lysine.

7. The mutant strain of a filamentous fungus of the genus *Trichoderma* according to claim 6, wherein the amino acid sequence constituting the beta-adaptin large subunit is any of the amino acid sequences represented by SEQ ID NOs: 2 to 10.

8. The mutant strain of a filamentous fungus of the genus *Trichoderma* according to claim 6, wherein the filamentous fungus of the genus *Trichoderma* is *Trichoderma* reesei.

9. A method of producing a protein, the method comprising a step of cultivating the mutant strain of a filamentous fungus of the genus *Trichoderma* according to claim 6.

10. A method of producing a cellulase, the method comprising a step of cultivating the mutant strain of a filamentous fungus of the genus *Trichoderma* according to claim 6.

* * * * *